United States Patent
Dabros et al.

(10) Patent No.: US 10,251,874 B2
(45) Date of Patent: Apr. 9, 2019

(54) CRYSTALLINE FORMS OF A JAK INHIBITOR COMPOUND

(71) Applicant: THERAVANCE BIOPHARMA R&D IP, LLC, South San Francisco, CA (US)

(72) Inventors: Marta Dabros, Foster City, CA (US); Venkat R. Thalladi, Foster City, CA (US); Jerry Nzerem, South San Francisco, CA (US); Melanie A. Kleinschek, San Francisco, CA (US); Glenn D. Crater, Raleigh, NC (US)

(73) Assignee: THERAVANCE BIOPHARMA R&D IP, LLC, South San Francisco, CA (US)

(*) Notice: Subject to any disclaimer, the term of this patent is extended or adjusted under 35 U.S.C. 154(b) by 0 days.

(21) Appl. No.: 15/966,452

(22) Filed: Apr. 30, 2018

(65) Prior Publication Data

US 2018/0311223 A1    Nov. 1, 2018

Related U.S. Application Data

(60) Provisional application No. 62/492,571, filed on May 1, 2017.

(51) Int. Cl.
| | |
|---|---|
| *A61K 31/4468* | (2006.01) |
| *A61K 9/00* | (2006.01) |
| *A61P 27/02* | (2006.01) |
| *A61P 11/08* | (2006.01) |
| *A61P 11/06* | (2006.01) |

(52) U.S. Cl.
CPC ........ *A61K 31/4468* (2013.01); *A61K 9/0075* (2013.01); *A61P 11/06* (2018.01); *A61P 11/08* (2018.01); *A61P 27/02* (2018.01)

(58) Field of Classification Search
CPC ................................................ A61K 31/4468
USPC ....................................................... 514/303
See application file for complete search history.

(56) References Cited

U.S. PATENT DOCUMENTS

| | | |
|---|---|---|
| 6,534,524 B1 | 3/2003 | Kania et al. |
| 6,884,890 B2 | 4/2005 | Kania et al. |
| 7,884,109 B2 | 2/2011 | Ohlmeyer et al. |
| 8,450,340 B2 | 5/2013 | Hood et al. |
| 8,575,336 B2 | 11/2013 | Coe et al. |
| 8,648,069 B2 | 2/2014 | Akritopoulou-Zanze |
| 8,895,544 B2 | 11/2014 | Coe et al. |
| 2005/0090529 A1 | 4/2005 | McAlpine et al. |
| 2015/0158864 A1 | 6/2015 | Thorarensen et al. |
| 2015/0329542 A1 | 11/2015 | Coe et al. |
| 2016/0289196 A1 | 10/2016 | Choi et al. |
| 2017/0121327 A1 | 5/2017 | Fatheree et al. |

FOREIGN PATENT DOCUMENTS

| | | |
|---|---|---|
| JP | 2010111624 A | 5/2010 |
| WO | 2005009389 A2 | 2/2005 |
| WO | 2010114971 A1 | 10/2010 |
| WO | 2013014567 A1 | 1/2013 |
| WO | 2015173683 A1 | 11/2015 |
| WO | 2016026078 A1 | 2/2016 |
| WO | 2017077283 A1 | 5/2017 |
| WO | 2017077288 A1 | 5/2017 |

OTHER PUBLICATIONS

Deobhakta et al., "Inflammation in retinal vein occlusion", International Journal of Inflammation, vol. 2013, 6 pages (2013).
Shchuko et al., "Intraocular cytokines in retinal vein occlusion and its relation to the efficiency of anti-vascular endothelial growth factor therapy", Indian Journal of Ophthalmology, 63: 905-911 (2015).
Yamamoto et al., "Mucosal inflammation in the terminal ileum of ulcerative colitis patients: Endoscopic findings and cytokine profiles", Digestive and Liver Disease, 40: 253-259 (2008).
Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chem., 59: 6690-6708 (2016).
Yano et al., "Ipilimumab augments antitumor activity of bispecific antibody-armed T cells", Journal of Translational Medicine, 12: 191 (2014).
Zeiser et al., "Ruxolitinib in corticosteroid-refractory graft-versus-host disease after allogeneic stem cell transplantation: a multi-center survey", Leukemia, 29(10): 2062-2068 (Oct. 2015).
Zhou et al., "Cytokines and Behcet's Disease", Autoimmunity Reviews, 11: 699-704 (2012).
Abcouwer, "Angiogenic factors and cytokines in diabetic retinopathy", J Clin Cell Immunol, Supplement 1: 1-12 (2013).
Bao et al., "The involvement of the JAK-STAT signaling pathway in chronic inflammatory skin disease atopic dermatitis", JAK-STAT, 2(3): e24137-1-e24137-8 (2013).
Berastegui et al., "BALF cytokines in different phenotypes of chronic lung allograft dysfunction in lung transplant patients", Clinical Transplantation, 31: e12898 (2017).

(Continued)

*Primary Examiner* — Taofiq A Solola
(74) *Attorney, Agent, or Firm* — Jeffrey A. Hagenah; Florence Jovic

(57) ABSTRACT

The present invention provides crystalline hydrates of the oxalate and succinate salts of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol. The invention also provides pharmaceutical compositions comprising such crystalline hydrates, methods of using such crystalline hydrates to treat respiratory and other diseases, and processes useful for preparing such crystalline oxalate and succinate hydrates.

23 Claims, 4 Drawing Sheets

(56) References Cited

OTHER PUBLICATIONS

Coghill et al., "Effector CD4+ T cells, the cytokines they generate, and GVHD: something old and something new", Blood, 117(12): 3268-3276 (Mar. 24, 2011).
Cottin, "Eosinophilic lung diseases", Clin Chest Med, 37: 535-556 (2016).
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease", World J Gastroenterol, 15(37): 4609-4614 (Oct. 7, 2009).
El-Hashemite et al., "Interferon-gamma-Jak-Stat signaling in pulmonary lymphangioleiomyomatosis and renal angiomyolipoma", Am J Respir Cell Mol Biol, 33: 227-230 (2005).
El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).
Fang et al., "Interleukin-6-572C/G polymorphism is associated with serum interleukin-6 levels and risk of idiopathic pulmonary arterial hypertension", Journal of the American Society of Hypertension, 11(3): 171-177 (2017).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Fenwick et al., "Effect of JAK inhibitors on release of CXCL9, CXCL10 and CXCL11 from human airway epithelial cells", PLOS One, 10(6): e0128757 (2015).
Foloppe et al., "Identification of a buried pocket for potent and selective inhibition of Chk1: Prediction and verification", Bioorganic & Medicinal Chemistry, 14: 1792-1804 (2006).
Funatsu et al., "Association of vitreous inflammatory factors with diabetic macular edema", Ophthalmology, 116: 73-79 (2009).
Gauthier et al., "Update on chronic lung allograft dysfunction", Curr Transplant Rep, 3(3): 185-191 (Sep. 2016).
Horai et al, "Cytokines in autoimmune uveitis", Journal of Interferon & Cytokine Research, 31(10): 733-744 (2011).
Huang et al., "Glycoprotein 130 inhibitor ameliorates monocrotalline-induced pulmonary hypertension in rats", Canadian Journal of Cardiology, 32: 1356.e1-1356.e10 (2016).
Jones et al., "Design and synthesis of a Pan-Janus kinase inhibitor clinical candidate (PF-06263276) suitable for inhaled and topical delivery for the treatment of inflammatory diseases of the lungs and skin", J. Med. Chem., 60: 767-786 (2017).
Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
McBride et al., "Design and structure-activity relationship of 3-benzimidazol-2-yl-1H-indazoles as inhibitors of receptor tyrosine kinases", Bioorganic & Medicinal Chemistry Letters, 16: 3595-3599 (2006).
McBride et al., "3-Benzimidazol-2-yl-1H-indazoles as potent c-ABL inhibitors", Bioorganic & Medicinal Chemistry Letters, 16: 3789-3792 (2006).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Owen et al., "Soluble mediators of diabetic macular edema: The diagnostic role of aqueous VEGF and cytokine levels in diabetic macular edema", Curr Diab Rep, 13(4): 476-480 (Aug. 2013).
Reimund et al., "Mucosal inflammatory cytokine production by intestinal biopsies in patients with ulcerative colitis and Crohn's disease", Journal of Clinical Immunology, 16(3): 144-150 (1996).
Shino et al., "The prognostic importance of CXCR3 chemokine during organizing pneumonia on the risk of chronic lung allograft dysfunction after lung transplantation", PLOS One, 12(7): e0180281 (2017).
Simov et al., "Structure-based design and development of (benz)imidazole pyridones as JAK1-selective kinase inhibitors", Bioorganic & Medicinal Chemistry Letters, 26: 1803-1808 (2016).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Tanaka et al., "New insight into mechanisms of pruritus from molecular studies on familial primary localized cutaneous amyloidosis", British Journal of Dermatology, 161: 1217-1224 (2009).
Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19: 908-911 (2009).
Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Abelson et al., "Sorting out the stats from the Jaks", Review of Ophthalmology, pp. 84-88 (Apr. 2013).
International Search Report and the Written Opinion for PCT/US2018/030144 dated Jul. 10, 2018.
U.S. Appl. No. 15/915,418, unpublished, Fatheree et al.
U.S. Appl. No. 15/915,434, unpublished, Fatheree et al.
U.S. Appl. No. 15/966,438, unpublished, Thalladi et al.
U.S. Appl. No. 15/966,467, unpublished, Fatheree et al.

CRYSTALLINE FORMS OF A JAK INHIBITOR COMPOUND

CROSS-REFERENCE TO RELATED APPLICATIONS

This application claims the benefit of U.S. Provisional Application No 62/492,571, filed on May 1, 2017, the disclosure of which is incorporated herein by reference in its entirety.

BACKGROUND OF THE INVENTION

Field of the Invention

The invention is directed to crystalline salt forms of a JAK inhibitor compound useful for treating respiratory and other diseases. The invention is also directed to pharmaceutical compositions comprising such compound, methods of using the salt forms to treat, for example, respiratory and ocular diseases, and processes and intermediates useful for preparing such crystalline salt forms.

State of the Art

Cytokines are intercellular signaling molecules which include chemokines, interferons, interleukins, lymphokines, and tumour necrosis factor. Cytokines are critical for normal cell growth and immunoregulation but also drive immune-mediated diseases and contribute to the growth of malignant cells. Elevated levels of many cytokines have been implicated in the pathology of a large number of disease or conditions, particularly those diseases characterized by inflammation. Many of the cytokines implicated in disease act through signaling pathways dependent upon the Janus family of tyrosine kinases (JAKs), which signal through the Signal Transducer and Activator of Transcription (STAT) family of transcription factors.

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with inflammation.

Asthma is a chronic disease of the airways for which there are no preventions or cures. The disease is characterized by inflammation, fibrosis, hyperresponsiveness, and remodeling of the airways, all of which contribute to airflow limitation. An estimated 300 million people worldwide suffer from asthma and it is estimated that the number of people with asthma will grow by more than 100 million by 2025. Although most patients can achieve control of asthma symptoms with the use of inhaled corticosteroids that may be combined with a leukotriene modifier and/or a long acting beta agonist, there remains a subset of patients with severe asthma whose disease is not controlled by conventional therapies. Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF). Inflammation of the airways is characteristic of other respiratory diseases in addition to asthma. Chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans are also respiratory tract diseases in which the pathophysiology is believed to be related to JAK-signaling cytokines.

Inflammation plays a prominent role in many ocular diseases, including uveitis, diabetic retinopathy, diabetic macular edema, dry eye disease, age-related macular degeneration, and atopic keratoconjunctivitis. Uveitis encompasses multiple intraocular inflammatory conditions and is often autoimmune, arising without a known infectious trigger. The condition is estimated to affect about 2 million patients in the US. In some patients, the chronic inflammation associated with uveitis leads to tissue destruction, and it is the fifth leading cause of blindness in the US. Cytokines elevated in uveitis patients' eyes that signal through the JAK-STAT pathway include IL-2, IL-4, IL-5, IL-6, IL-10, IL-23, and IFN-γ. (Horai and Caspi, *J Interferon Cytokine Res*, 2011, 31, 733-744; Ooi et al, *Clinical Medicine and Research*, 2006, 4, 294-309). Existing therapies for uveitis are often suboptimal, and many patients are poorly controlled. Steroids, while often effective, are associated with cataracts and increased intraocular pressure/glaucoma.

Diabetic retinopathy (DR) is caused by damage to the blood vessels in the retina. It is the most common cause of vision loss among people with diabetes. Angiogenic as well as inflammatory pathways play an important role in the disease. Often, DR will progress to diabetic macular edema (DME), the most frequent cause of visual loss in patients with diabetes. The condition is estimated to affect about 1.5 million patients in the US alone, of whom about 20% have disease affecting both eyes. Cytokines which signal through the JAK-STAT pathway, such as IL-6, as well as other cytokines, such as IP-10 and MCP-1 (alternatively termed CCL2), whose production is driven in part by JAK-STAT pathway signaling, are believed to play a role in the inflammation associated with DR/DME (Abcouwer, *J Clin Cell Immunol*, 2013, Suppl 1, 1-12; Sohn et al., *American Journal of Opthalmology*, 2011, 152, 686-694; Owen and Hartnett, *Curr Diab Rep*, 2013, 13, 476-480; Cheung et al, *Molecular Vision*, 2012, 18, 830-837; Dong et al, *Molecular Vision*, 2013, 19, 1734-1746; Funatsu et al, *Ophthalmology*, 2009, 116, 73-79). The existing therapies for DME are suboptimal: intravitreal anti-VEGF treatments are only effective in a fraction of patients and steroids are associated with cataracts and increased intraocular pressure.

Dry eye disease (DED) is a multifactorial disorder that affects approximately 5 million patients in the US. Ocular surface inflammation is believed to play an important role in the development and propagation of this disease. Elevated levels of cytokines such as IL-1, IL-2, IL-4, IL-5, IL-6, and IFN-γ have been noted in the ocular fluids of patients with DED. (Stevenson et al, *Arch Ophthalmol*, 2012, 130, 90-100), and the levels often correlated with disease severity. Age-related macular degeneration and atopic keratoconjunctivitis are also thought to be associated with JAK-dependent cytokines.

Commonly assigned U.S. application Ser. No. 15/341, 226, filed Nov. 2, 2016 discloses diamino compounds useful as JAK inhibitors. In particular, the compound 5-ethyl-2- fluoro-4-(3-(5-(1-methylpiperidin-4-yl)-4,5,6,7-tetrahydro-1H-imidazo[4,5-c]pyridin-2-yl)-1H-indazol-6-yl)phenol (compound 1)

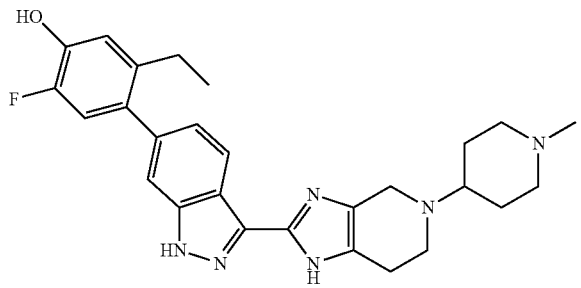

is specifically disclosed in the application as a potent pan-JAK inhibitor.

To effectively use this compound as a therapeutic agent, it would be desirable to have a crystalline solid-state salt form. For example, it would be highly desirable to have a physical form that is thermally stable at reasonably high temperature, thereby facilitating processing and storage of the material. Crystalline solids are generally preferred over amorphous forms, for enhancing purity and stability of the manufactured product. However, the formation of crystalline forms of organic compounds is highly unpredictable. No reliable methods exist for predicting which, if any, form of an organic compound will be crystalline. Moreover, no methods exist for predicting which, if any, crystalline form will have the physically properties desired for use as pharmaceutical agents.

No crystalline salt forms of compound 1 have previously been reported. Accordingly, a need exists for crystalline salt forms of compound 1.

SUMMARY OF THE INVENTION

The present invention provides crystalline hydrates of the oxalate and succinate salts of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1).

The crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol has been found to have a melting temperature in the range of about 266° C. to about 276° C. and to exhibit total moisture uptake of about 1% when exposed to a range of relative humidity between about 30% and about 90% at room temperature.

The crystalline hydrate of the succinate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol has been found to have a melting temperature in the range of about 180° C. to about 190° C. and to exhibit total moisture uptake of about 2% when exposed to a range of relative humidity between about 5% and about 90% at room temperature.

Among other uses, the crystalline solid forms of the invention are expected to be useful for preparing pharmaceutical compositions for treating or ameliorating disease amenable to treatment with a JAK inhibitor, in particular respiratory disease. Accordingly, in another of its composition aspects, the invention provides a pharmaceutical composition comprising a pharmaceutically-acceptable carrier and an active agent selected from the crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol and the crystalline hydrate of the succinate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol.

The invention also provides a method of treating respiratory disease, in particular, asthma, in a mammal, the method comprising administering to the mammal a crystalline solid form or a pharmaceutical composition of the invention. In separate and distinct aspects, the invention also provides synthetic processes useful for preparing the crystalline forms of the invention.

The invention further provides a method of treating an ocular inflammatory disease in a mammal, the method comprising administering to the eye of the mammal, a crystalline solid form or a pharmaceutical composition of the invention.

The invention also provides a crystalline solid form of the invention as described herein for use in medical therapy, as well as the use of a crystalline solid form of the invention in the manufacture of a formulation or medicament for treating respiratory disease in a mammal.

BRIEF DESCRIPTION OF THE DRAWINGS

Various aspects of the present invention are illustrated by reference to the accompanying drawings.

DETAILED DESCRIPTION OF THE INVENTION

Definitions

Figure 1:
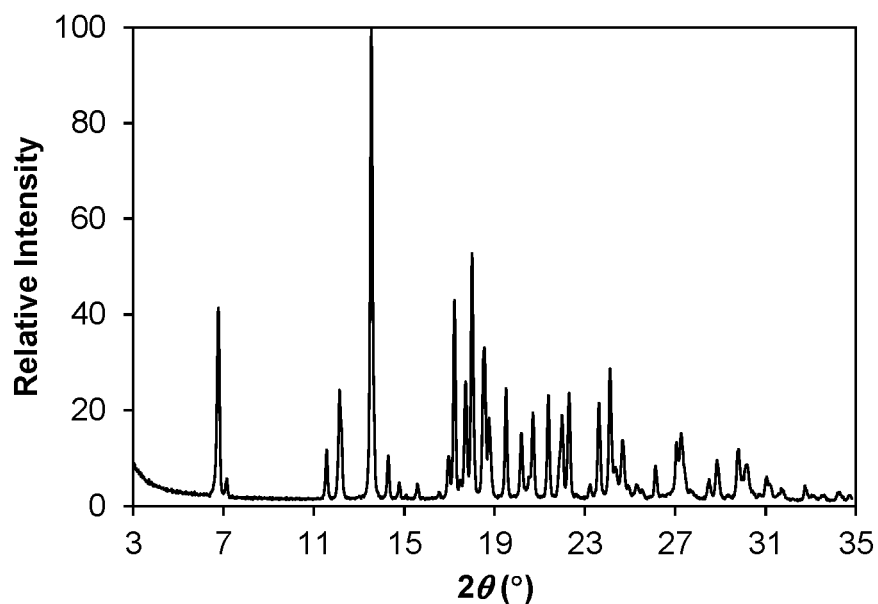
FIG. 1 shows a powder x-ray diffraction (PXRD) pattern of the crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (hereinafter 'oxalate hydrate').

When describing this invention including its various aspects and embodiments, the following terms have the following meanings, unless otherwise indicated.

The term "therapeutically effective amount" means an amount sufficient to effect treatment when administered to a patient in need of treatment.

The term "treating" or "treatment" means preventing, ameliorating or suppressing the medical condition, disease or disorder being treated (e.g., a respiratory disease) in a patient (particularly a human); or alleviating the symptoms of the medical condition, disease or disorder.

The term "hydrate" means a complex or aggregate, typically in crystalline form, formed by molecules of water and the compound of the invention where the ratio of water molecules to compound molecules may be less than 1:1 or more than 1:1.

The term "about" means±5 percent of the specified value.

It must be noted that, as used in the specification and appended claims, the singular forms "a", "an", "one", and "the" may include plural references, unless the content clearly dictates otherwise.

Naming Convention

Compound 1 is designated as 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol according to IUPAC conventions as implemented in ChemDraw software (PerkinElmer, Inc., Cambridge, Mass.).

Furthermore, the imidazo portion of the tetrahydroimidazopyridine moiety in the structure of compound 1 exists in tautomeric forms, illustrated below for a fragment of the compound of Example 1

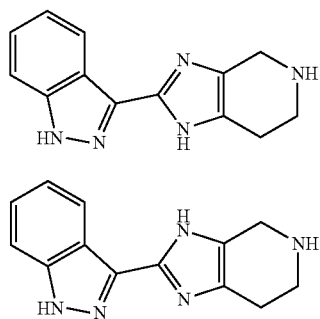

According to the IUPAC convention, these representations give rise to different numbering of the atoms of the imidazole portion: 2-(1H-indazol-3-yl)-4,5,6,7-tetrahydro-1H-imidazo[4,5-c]pyridine (structure A) vs. 2-(1H-indazol-3-yl)-4,5,6,7-tetrahydro-3H-imidazo[4,5-c]pyridine (structure B). It will be understood that although structures are shown, or named, in a particular form, the invention also includes the tautomer thereof.

Crystalline Forms of the Invention

In one aspect, the invention provides the crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1).

In one aspect, the crystalline oxalate hydrate is characterized by a powder X-ray diffraction (PXRD) pattern having significant diffraction peaks, among other peaks, at 2θ values of 6.77±0.20, 12.13±0.20, 13.54±0.20, 17.23±0.20, and 18.00±0.20. The crystalline oxalate hydrate may be further characterized by a PXRD pattern having two or more additional diffraction peaks, including three or more additional diffraction peaks at 2θ values selected from 11.56±0.20, 14.29±0.20, 19.51±0.20, 21.38±0.20, and 23.63±0.20. In another aspect, the crystalline oxalate hydrate is characterized by a PXRD pattern having diffraction peaks at 2θ values of 6.77±0.20, 11.56±0.20, 12.13±0.20, 13.54±0.20, 14.29±0.20, 17.23±0.20, 18.00±0.20, 19.51±0.20, 21.38±0.20, and 23.63±0.20.

As is well known in the field of powder X-ray diffraction, peak positions of PXRD spectra are relatively less sensitive to experimental details, such as details of sample preparation and instrument geometry, than are the relative peak heights. Thus, in one aspect, the crystalline oxalate hydrate is characterized by a powder x-ray diffraction pattern in which the peak positions are substantially in accordance with those shown in FIG. 1.

Figure 2:
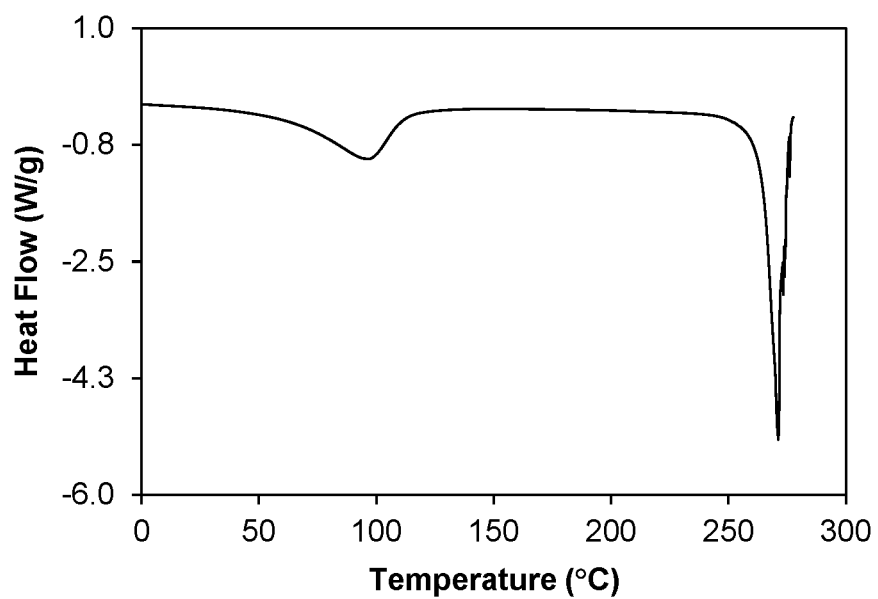
FIG. 2 shows a differential scanning calorimetry (DSC) thermogram of the oxalate hydrate of the invention.
Figure 3:
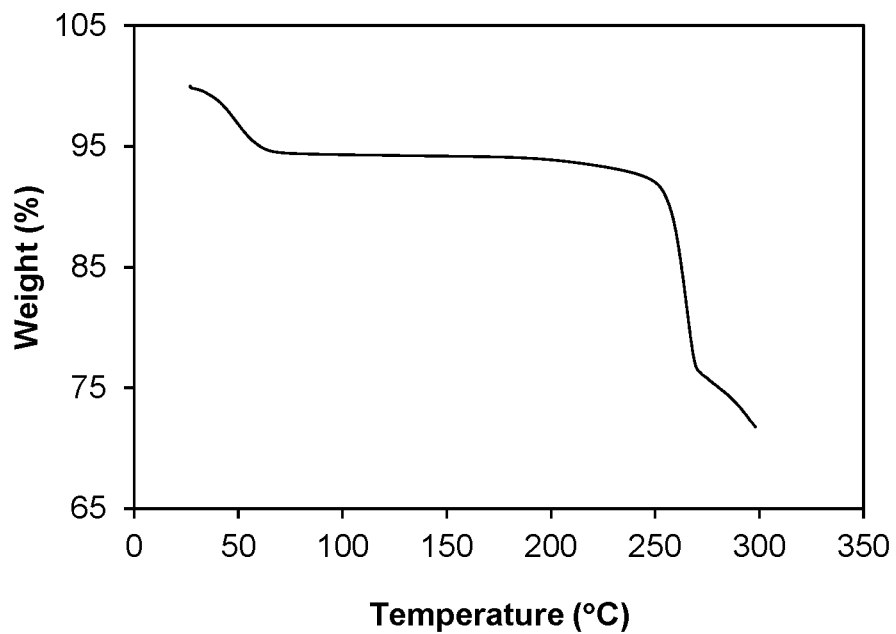
FIG. 3 shows a thermal gravimetric analysis (TGA) plot of the oxalate hydrate of the invention.

In another aspect, the crystalline oxalate hydrate is characterized by its behavior when exposed to high temperature. As demonstrated in FIG. 2, the differential scanning calorimetry (DSC) trace recorded at a heating rate of 10° C. per minute exhibits a desolvation endotherm with an onset at about 59° C. and a peak at about 97° C. and a peak in endothermic heat flow, identified as a melt transition, in the range of about 266° C. to about 276° C. including between about 268° C. and about 273° C. The thermal gravimetric analysis (TGA) trace of FIG. 3 shows a desolvation onset at a temperature of about 26° C. and a decomposition onset at a temperature of about 250° C. Taken together, the DSC and TGA traces suggest the melt transition is accompanied by decomposition. The TGA profile shows a weight loss of about 5.5% between about 25° C. and about 75° C.

Figure 4:
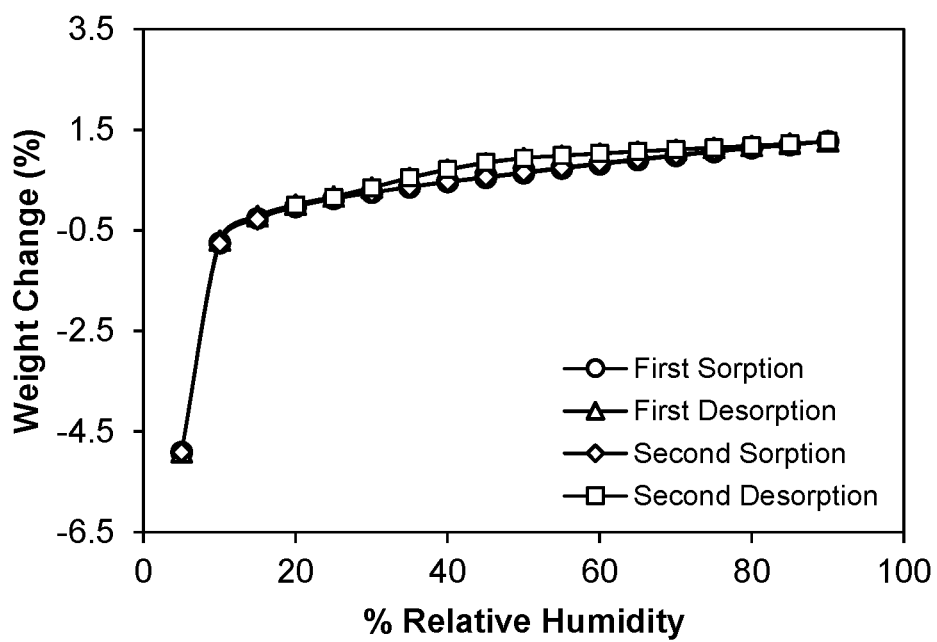
FIG. 4 shows a dynamic moisture sorption (DMS) isotherm of the oxalate hydrate of the invention observed at a temperature of about 25° C.

The present crystalline oxalate hydrate has been demonstrated to have a reversible sorption/desorption profile with a slight propensity for hygroscopicity. The oxalate hydrate exhibited total moisture uptake of about 1% when exposed to a range of relative humidity between about 30% and about 90% at room temperature as shown in FIG. 4. A reversible hydration/dehydration transition was observed between about 0% and 15% relative humidity. No hysteresis was observed in two cycles of sorption and desorption.

In another aspect, the invention provides the crystalline hydrate of the succinate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1)

Figure 5:
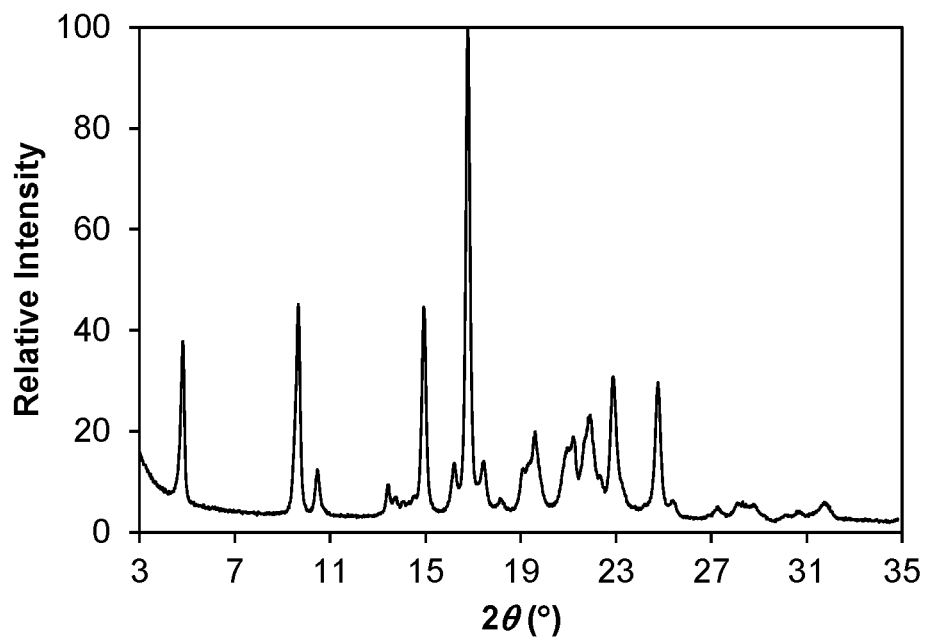
FIG. 5 shows a powder x-ray diffraction (PXRD) pattern of the crystalline succinate hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (hereinafter 'succinate hydrate').

In one aspect, the crystalline succinate hydrate is characterized by a powder X-ray diffraction (PXRD) pattern having significant diffraction peaks, among other peaks, at 2θ values of 4.81±0.20, 9.66±0.20, 14.93±0.20, and 16.78±0.20. The crystalline succinate hydrate may be further characterized by a PXRD pattern having two or more additional diffraction peaks, including three or more additional diffraction peaks at 2θ values selected from 10.46±0.20, 16.21±0.20, 17.45±0.20, 22.87±0.20, and 24.77±0.20. In another aspect, the crystalline oxalate hydrate is characterized by a PXRD pattern having diffraction peaks at 2θ values of 4.81±0.20, 9.66±0.20, 10.46±0.20, 14.93±0.20, 16.21±0.20, 16.78±0.20, 17.45±0.20, 22.87±0.20, and 24.77±0.20. In yet another aspect, the crystalline succinate hydrate is characterized by a powder x-ray diffraction pattern in which the peak positions are substantially in accordance with those shown in FIG. 5.

Figure 6:
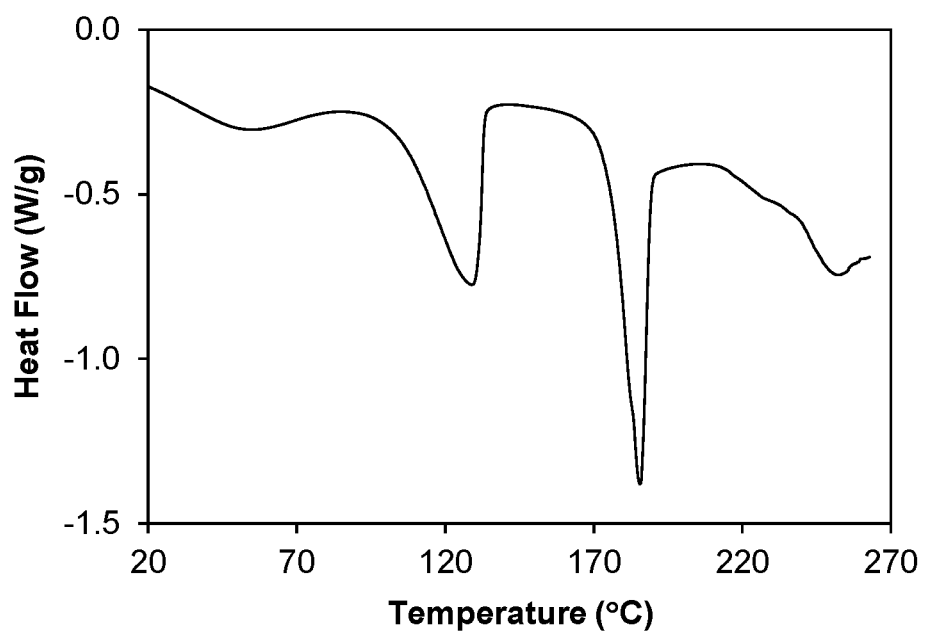
FIG. 6 shows a differential scanning calorimetry (DSC) thermogram of the succinate hydrate of the invention.
Figure 7:
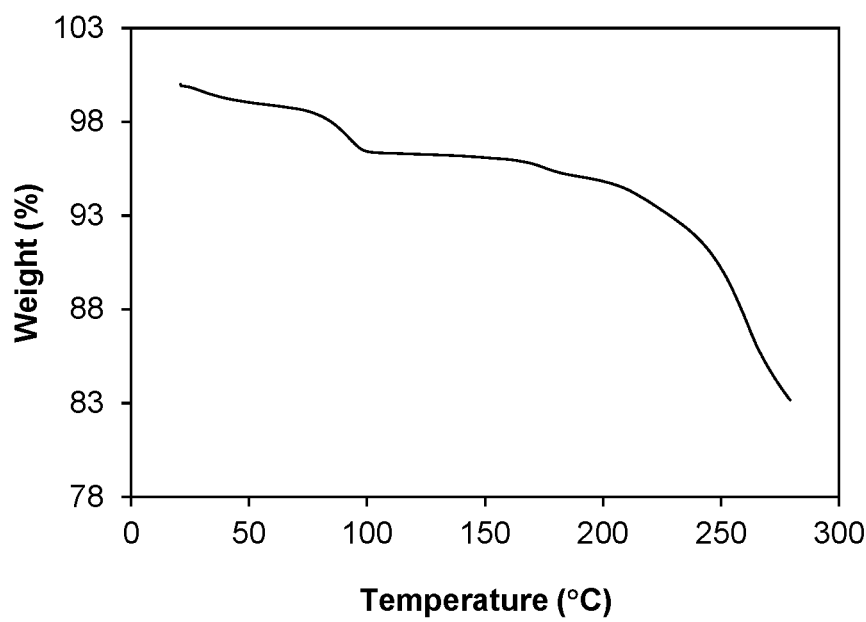
FIG. 7 shows a thermal gravimetric analysis (TGA) plot of the succinate hydrate of the invention.

The crystalline succinate hydrate is also characterized by its behavior when exposed to high temperature. As demonstrated in FIG. 6, the differential scanning calorimetry (DSC) trace recorded at a heating rate of 10° C. per minute exhibits two desolvation endotherms: one with an onset at about 20° C. and a peak at about 50° C. and a second desolvation endotherm with an onset at about 103° C. and a peak at about 129° C. The DSC trace further exhibits a peak in endothermic heat flow, identified as a melt transition, in the range of about 180° C. to about 190° C. including between about 183° C. and about 188° C. The thermal gravimetric analysis (TGA) trace of FIG. 7 shows a decomposition onset at a temperature of about 200° C.

Figure 8:
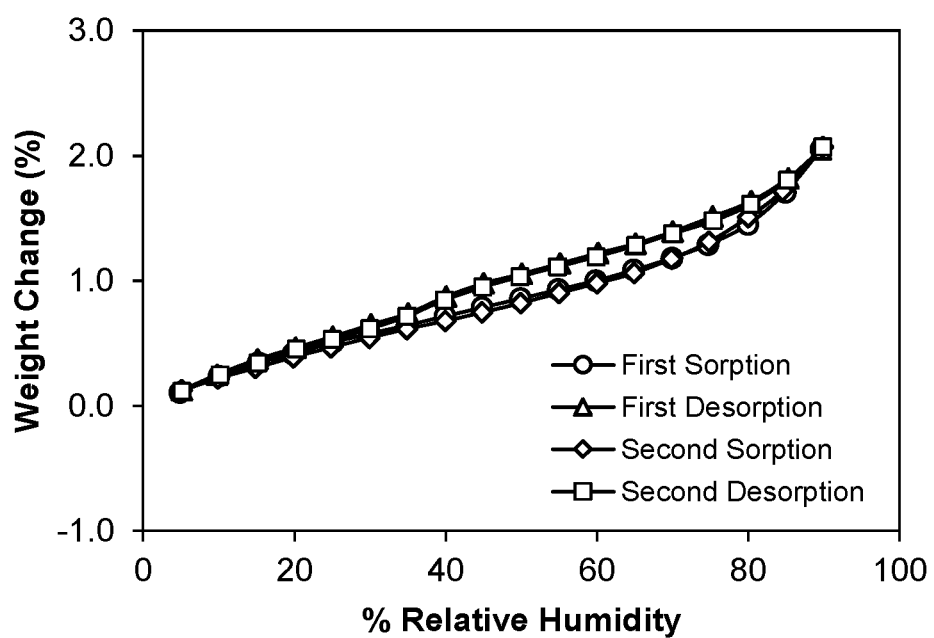
FIG. 8 shows a dynamic moisture sorption (DMS) isotherm of the succinate hydrate of the invention observed at a temperature of about 25° C.

The crystalline succinate hydrate has been demonstrated to have a reversible sorption/desorption profile with a slight propensity for hygroscopicity. The succinate hydrate exhibited total moisture uptake of about 2% when exposed to a range of relative humidity between about 5% and about 90% at room temperature as shown in FIG. 8. No hysteresis was observed in two cycles of sorption and desorption.

Synthetic Procedures

Compound 1, can be prepared from readily available starting materials using the procedures described in the Examples below, or using the procedures described in the commonly-assigned U.S. application listed in the Background section of this application.

The crystalline oxalate hydrate of the invention is conveniently prepared by dissolving an equimolar mixture of compound 1 and oxalic acid in a 1:1 mixture of tetrahydrofuran and water at room temperature followed by the addition of a 1:1:2 mixture of tetrahydrofuran:water:acetonitrile, as an antisolvent to produce a suspension. The resulting reaction mixture is stirred for about one day at room temperature, washed with acetonitrile, and dried to provide the crystalline hydrate form.

The present crystalline succinate hydrate may be prepared by a three stage process. First, an equimolar mixture of compound 1 and succinic acid is suspended in isopropanol and stirred for about one day at room temperature. The resulting solids are filtered, washed with isopropanol, and dried to provide a first intermediate crystalline solid. Second, the isolated first intermediate crystalline solid is dried at about 150° C. for about 30 minutes to provide a second intermediate crystalline solid. Third, the second intermediate solid is equilibrated under about 80% to 90% relative humidity for about one day at room temperature to provide the crystalline succinate hydrate form.

Accordingly in a method aspect, the invention provides a method of preparing the crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol, the method comprising (a) dissolving a 1:1 mixture of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol: oxalic acid in a 1:1 mixture of tetrahydrofuran:water at room temperature, (b) adding a 1:1:2 mixture of tetrahydrofuran:water:acetonitrile to produce a suspension, (c) stirring the suspension for about one day, and (d) isolating the crystalline oxalate hydrate from the suspension.

Pharmaceutical Compositions

The crystalline solid forms of the invention are typically used in the form of a pharmaceutical composition or formulation. Such pharmaceutical compositions may advantageously be administered to a patient by inhalation. In addition, pharmaceutical compositions may be administered by any acceptable route of administration including, but not limited to, oral, topical (including transdermal), rectal, nasal, and parenteral modes of administration.

Accordingly, in one of its compositions aspects, the invention is directed to a pharmaceutical composition comprising a pharmaceutically-acceptable carrier or excipient and a crystalline oxalate hydrate or crystalline succinate hydrate of compound 1. Optionally, such pharmaceutical compositions may contain other therapeutic and/or formulating agents if desired. When discussing compositions and uses thereof, the crystalline solid forms of the invention may also be referred to herein as the "active agent".

The pharmaceutical compositions of the invention typically contain a therapeutically effective amount of the crystalline forms of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Maryland (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a crystalline solid form of the invention in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the invention; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another particular aspect, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 µg/mL to about 20 mg/mL of a compound of the invention and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat Softmist Inhaler (Boehringer Ingelheim); the AERx Pulmonary Delivery System (Aradigm Corp.); the PARI LC Plus Reusable Nebulizer (Pari GmbH); and the like.

In yet another aspect, the pharmaceutical compositions of the invention may alternatively be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the pharmaceutical compositions of the invention.

The crystalline solid forms may also be formulated as a sterile aqueous suspension or solution for ocular injection. Useful excipients that may be included in such an aqueous formulation include polysorbate 80, carboxymethylcellulose, potassium chloride, calcium chloride, magnesium chloride, sodium acetate, sodium citrate, histidine, α-α-trehalose dihydrate, sucrose, polysorbate 20, hydroxypropyl-β-cyclodextrin, and sodium phosphate. Benzyl alcohol may serve as a preservative and sodium chloride may be included to adjust tonicity. In addition, hydrochloric acid and/or sodium hydroxide may be added to the solution for pH adjustment. Aqueous formulations for ocular injection may be prepared as preservative-free.

Alternative formulations may also include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present invention.

Dry Powder Composition

A micronized solid form of the invention (1 g) is blended with milled lactose (25 g). This blended mixture is then loaded into individual blisters of a peelable blister pack in an amount sufficient to provide between about 0.1 mg to about 4 mg of the compound of formula I per dose. The contents of the blisters are administered using a dry powder inhaler.

Dry Powder Composition

A micronized solid form of the invention (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound of formula I per dose.

Metered-Dose Inhaler Composition

A micronized solid form of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μ. The micronized composition is then loaded into metered-dose inhaler cartridges containing pressurized 1,1,1,2-tetrafluoroethane in an amount sufficient to provide about 0.1 mg to about 4 mg of the compound of formula I per dose when administered by the metered dose inhaler.

Nebulizer Composition

A solid form of the invention (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of the compound of formula I per dose.

Aqueous Formulation for Ocular Injection

Each mL of a sterile aqueous suspension includes from 5 mg to 50 mg of a solid form of the invention, sodium chloride for tonicity, 0.99% (w/v) benzyl alcohol as a preservative, 0.75% carboxymethylcellulose sodium, and 0.04% polysorbate. Sodium hydroxide or hydrochloric acid may be included to adjust pH to 5 to 7.5.

Aqueous Formulation for Ocular Injection

A sterile preservative-free aqueous suspension includes from 5 mg/mL to 50 mg/mL of a solid form of the invention in 10 mM sodium phosphate, 40 mM sodium chloride, 0.03% polysorbate 20, and 5% sucrose.

Utility

The present compound, 5-ethyl-2-fluoro-4-(3-(5-(1-methylpiperidin-4-yl0-4,5,6,7-tetrahydro-1H-imidazo[4,5-c]pyridin-2-yl)-1H-indazol-6-yl)phenol, (compound 1), has been shown to be a potent inhibitor of the JAK family of enzymes: JAK1, JAK2, JAK3, and TYK2.

Respiratory Diseases

In addition, as described in the assays below, compound 1 has demonstrated potent inhibition of pro-inflammatory and pro-fibrotic cytokines implicated in asthma and other respiratory diseases. The absorption and distribution of the compound has been profiled in preclinical assays. In mouse the compound exhibited exposure in lung about 55 times greater than the exposure in plasma. Importantly, the concentration of compound 1 in the mouse lung has been shown to correlate with a predicted pharmacodynamic effect of JAK enzyme inhibition. In particular, the compounds has been shown to inhibit an effect of the pro-inflammatory cytokine IL-13 in mouse lung tissue. Specifically, the compound demonstrated inhibition of IL-13-induced phosphorylation of STAT6 in lung tissue which provides evidence of local lung JAK target engagement in vivo. This effect has been observed when the pro-inflammatory cytokine IL-13 is administered 4 hours after administration of the test compound, providing further evidence of significant retention in the lung.

The anti-inflammatory activity of JAK inhibitors has been robustly demonstrated in preclinical models of asthma (Malaviya et al., *Int Immunopharmacol*, 2010, 10, 829,-836; Matsunaga et al., *Biochem and Biophys Res Commun*, 2011, 404, 261-267; Kudlacz et al., *Eur J Pharmacol*, 2008, 582, 154-161.) Accordingly, the compounds of the invention are expected to be useful for the treatment of inflammatory respiratory disorders, in particular, asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. The present compounds, therefore, are also expected to be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema and bronchiolitis obliterans. As described above, for treatment of respiratory diseases, solid forms are particular useful for administration by inhalation.

In one aspect, therefore, the invention provides a method of treating a respiratory disease in a mammal (e.g., a human), the method comprising administering to the mammal a therapeutically-effective amount of a compound of the invention or of a pharmaceutical composition comprising a pharmaceutically-acceptable carrier and a solid form of the invention.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema or bronchiolitis obliterans. In another aspect, the respiratory disease is asthma or chronic obstructive pulmonary disease. In another aspect, the solid forms of the invention are administered by inhalation.

The invention further provides a method of treating asthma in a mammal, the method comprising administering to the mammal a solid form of the invention or a pharmaceutical composition comprising a pharmaceutically-acceptable carrier and a solid form of the invention.

When used to treat asthma, the compounds of the invention will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

In addition to having demonstrated potent inhibition of cytokines associated with inflammation, compound 1 has demonstrated inhibition of T cell activation and activity in rodent lung eosinophilia and neutrophilia assays. Therefore, the solid forms of the invention are believed to useful for the treatment of additional respiratory conditions.

The additional respiratory conditions include lung infections, helminthic infections, pulmonary arterial hypertension, sarcoidosis, lymphangioleiomyomatosis, bronchiectasis, and infiltrative pulmonary disease. The solid forms are also believed to be useful for the treatment of drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Loffler syndrome, bronchiolitis obliterans organizing pneumonia, and immune-checkpoint-inhibitor induced pneumonitis.

JAK-signaling cytokines also play a major role in the activation of T cells, a sub-type of immune cells that is central to many immune processes. Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., Curr Transplant Rep., 2016, 3(3), 185-191). CLAD is poorly responsive to treatment and therefore, there remains a need for effective compounds capable of preventing or treating this condition.

Several JAK-dependent cytokines such as IFNγ and IL-5 are up-regulated in CLAD and lung transplant rejection (Berastegui et al, Clin Transplant. 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, PLOS One, 2017, 12 (7), e0180281). Systemic JAK inhibition has been shown to be effective in kidney transplant rejection (Vicenti et al., American Journal of Transplantation, 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, Leukemia, 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD.

Accordingly, the invention further provides a method of treating the additional respiratory conditions described above in a mammal, the method comprising administering to the mammal a solid form of the invention or a pharmaceutical composition comprising a pharmaceutically-acceptable carrier and a solid form of the invention.

Ocular Diseases

Many ocular diseases have been shown to be associated with elevations of proinflammatory cytokines that rely on the JAK-STAT pathway. Since the compound of the invention exhibits potent inhibition at all four JAK enzymes, it is expected to potently inhibit the signaling and pathogenic effects of numerous cytokines (such as IL-6, IL-2 and IFN-γ), that signal through JAK, as well as to prevent the increase in other cytokines (such as MCP-1 and IP-10), whose production is driven by JAK-STAT pathway signaling.

In particular, Compound 1 exhibited $pIC_{50}$ values of 6.7 or greater ($IC_{50}$ values of 200 nM or less) for inhibition of IL-2, IL-4, IL-6, and IFNγ signaling in the cellular assays described in Assays 3 to 7, including assays registering inhibition of the downstream effects of cytokine elevation.

The pharmacokinetic study of Assay 12 demonstrated sustained exposure in rabbit eyes after a single intravitreal injection of a suspension of the crystalline compound 1 of example 2, and a concentration in plasma at least three orders of magnitude lower than that observed in vitreous tissue. Assays 13 and 14 demonstrated a pharmacodynamic effect of the compound in rats and rabbits.

The solid forms of the invention, therefore, are expected to be beneficial in a number of ocular diseases that include, but are not limited to, uveitis, diabetic retinopathy, diabetic macular edema, dry eye disease, age-related macular degeneration, and atopic keratoconjunctivitis.

In particular, uveitis (Horai and Caspi, J Interferon Cytokine Res, 2011, 31, 733-744), diabetic retinopathy (Abcouwer, J Clin Cell Immunol, 2013, Suppl 1, 1-12), diabetic macular edema (Sohn et al., American Journal of Opthalmology, 2011, 152, 686-694), dry eye disease (Stevenson et al, Arch Ophthalmol, 2012, 130, 90-100), and age-related macular degeneration (Knickelbein et al, Int Ophthalmol Clin, 2015, 55(3), 63-78) are characterized by elevation of certain pro-inflammatory cytokines that signal via the JAK-STAT pathway. Accordingly, the solid forms of the invention may be able to alleviate the associated ocular inflammation and reverse disease progression or provide symptom relief.

Retinal vein occlusion (RVO) is a highly prevalent visually disabling disease. Obstruction of retinal blood flow can lead to damage of the retinal vasculature, hemorrhage, and tissue ischemia. Although the causes for RVO are multifactorial, both vascular as well as inflammatory mediators have been shown to be important (Deobhakta et al, International Journal of Inflammation, 2013, article ID 438412). Cytokines which signal through the JAK-STAT pathway, such as IL-6 and IL-13, as well as other cytokines, such as MCP-1, whose production is driven in part by JAK-STAT pathway signaling, have been detected at elevated levels in ocular tissues of patients with RVO (Shchuko et al, Indian Journal of Ophthalmology, 2015, 63(12), 905-911). Accordingly, the solid forms of the invention may be able to alleviate the associated ocular inflammation and reverse disease progression or provide symptom relief in this disease. While many patients with RVO are treated by photocoagulation, this is an inherently destructive therapy. Anti-VEGF agents are also used, but they are only effective in a fraction of patients. Steroid medications that reduce the level of inflammation in the eye (Triamcinolone acetonide and dexamethasone implants) have also been shown to provide beneficial results for patients with certain forms of RVO, but they have also been shown to cause cataracts and increased intraocular pressure/glaucoma.

In one aspect, therefore, the invention provides a method of treating an ocular disease in a mammal, the method comprising administering a solid form of the invention to the eye of the mammal. In one aspect, the ocular disease is uveitis, diabetic retinopathy, diabetic macular edema, dry eye disease, age-related macular degeneration, or atopic keratoconjunctivitis. In one aspect, the ocular disease is retinal vein occlusion.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
CPME=cyclopentyl methyl ether
DCM=dichloromethane
DIPEA=N,N-diisopropylethylamine
DMAc=dimethylacetamide
DMF=N,N-dimethylformamide
EtOAc=ethyl acetate
h=hour(s)
IPAc=isopropylacetate
KOAc=potassium acetate
MeOH=methanol
MeTHF=2-methyltetrahydrofuran
min=minute(s)
MTBE=methyl tent-butyl ether
NMP=N-methyl-2-pyrrolidone
Pd(amphos)$_2$Cl$_2$=bis(di-tert-butyl(4-dimethylaminophenyl)-phosphine)dichloropalladium(II)
Pd(dppf)Cl$_2$=dichloro(1,1'-bis(diphenylphosphino)-ferrocene)dipalladium(II)
Pd(PPh$_3$)$_4$=tetrakis(triphenylphosphine)palladium(0)
Pd(t-Bu$_3$P)$_2$=bis(tri-tert-butylphosphine) palladium(0)
RT=room temperature
TEA=triethylamine
TFA=trifluoroacetic acid
THF=tetrahydrofuran
bis(pinacolato)diboron=4,4,5,5,4',4',5',5'-octamethyl-[2,2]bi[[1,3,2]dioxaborolanyl]

Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions

Column: C18, 5 μm. 21.2×150 mm or C18, 5 μm 21×250 or C14, 5 μm 21×150 mm

Column temperature: Room Temperature

Flow rate: 20.0 mL/min

Mobile Phases: A=Water+0.05% TFA B=ACN+0.05% TFA,

Injection volume: (100-1500 μL)

Detector wavelength: 214 nm

Crude compounds were dissolved in 1:1 water:acetic acid at about 50 mg/mL . A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions

Method A

Column: Agilent Zorbax Bonus-RP C18, 150×4.60 nm, 3.5 micron

Column temperature: 40° C.

Flow rate: 1.5 mL/min

Injection volume: 5 μL

Sample preparation: Dissolve in 1:1 ACN:1 M HCl

Mobile Phases: A=Water: TFA (99.95:0.05) B=ACN:TFA (99.95:0.05)

Detector wavelength: 254 nm and 214 nm

Gradient: 26 min total (time (min)/ % B): 0/5, 18/90, 22/90, 22.5/90, 26/5

Method B

Column: Agilent Poroshell 120 Bonus-RP, 4.6×150 mm, 2.7 μm

Column temperature: 30° C.

Flow rate: 1.5 mL/min

Injection volume: 10 μL

Mobile Phases: A=ACN:Water:TFA (2:98:0.1) B=ACN:Water:TFA (90:10:0.1)

Sample preparation: Dissolve in Mobile phase B

Detector wavelength: 254 nm and 214 nm

Gradient: 60 min total (time (min)/ % B): 0/0, 50/100, 55/100, 55.1/0, 60/0

Method C

Column: Agilent Poroshell 120 Bonus-RP, 4.6×150 mm, 2.7 μm

Column temperature: 30° C.

Flow rate: 1.5 mL/min

Injection volume: 10 μL

Mobile Phases: A=ACN:Water:TFA (2:98:0.1) B=ACN:Water:TFA (90:10:0.1)

Sample preparation: Dissolve in Mobile phase B (0.15 mL) then dilute with Mobile phase A (0.85 mL)
Detector wavelength: 245 nm
Gradient: 46 min total (time (min)/ % B): 0/0, 25/50, 35/100,40/100, 40.1/0, 46/0

Preparation 1: 1-benzyl-4-imino-1,4-dihydropyridin-3-amine

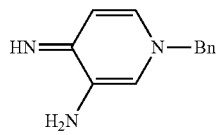

A mixture of pyridine-3,4-diamine (445 g, 4.078 mol) and ACN (11.0 L) was stirred for 80 min from 25° C. to 15° C. Benzyl bromide (485 mL, 4.078 mol) was added over 20 min and the reaction mixture was stirred at 20° C. overnight. The reaction mixture was cooled to 10° C. and filtered. To the reactor was added ACN (3 L), which was cooled to 10° C. The cake was washed with the reactor rinse and washed again with ACN (3 L) warmed to 25° C. The solid was dried on the filter for 24 h under nitrogen, at 55° C. under vacuum for 2 h and then at RT overnight and for 4 d to provide the HBr salt of the title compound (1102.2 g, 3.934 mol, 96% yield). HPLC Method A Retention time 4.12 min.

Preparation 2: 5-Benzyl-2-(6-bromo-1H-indazol-3-yl)-5H-imidazo[4,5-c]pyridine

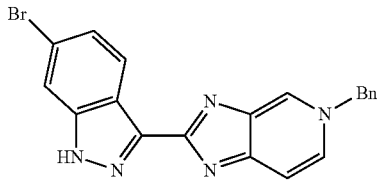 [SMILES: Brc1ccc2c(-c3nc4ccn(Cc5ccccc5)cc-4n3)n[nH]c2c1]

(a) 5-Benzyl-2-(6-bromo-1H-indazol-3-yl)-5H-imidazo[4,5-c]pyridine

A solution of 6-bromo-1H-indazole-3-carbaldehyde (550 g, 2.444 mol), 1-benzyl-4-imino-1,4-dihydropyridin-3-amine HBr (721 g, 2.333 mol) and DMAc (2.65 L) was stirred for 60 min and sodium bisulfite (257 g, 2.468 mol) was added. The reaction mixture was heated to 135° C. and held for 3 h, and allowed to cool to 20° C. and held at 20° C. overnight. Acetonitrile (8 L) was added and the reaction mixture was stirred for 4 h at 15° C. The slurry was filtered on a pressure filter at medium filtration rate. To the reactor was added ACN (1 L) The cake was washed with the ACN reactor wash and dried under nitrogen overnight and then under vacuum at 50° C. for 24 h to provide the HBr salt of the title compound (1264 g, 2.444 mol, 100% yield, 94% purity) as a dense wet beige/brown solid. HPLC Method A Retention time 8.77 min.

A mixture of the product of the previous step (1264 g, 2.444 mol), MeTHF (6 L) and water (2.75 L) was heated to 65° C. and sodium hydroxide 50 wt % (254 g, 3.177 mol) was added over 5 min and the reaction mixture was stirred at 65° C. for 1 h, cooled to RT, then to 5° C. and held for 2 h. The slurry was filtered and the reactor and cake were washed with MeTHF (1 L). The resulting beige to yellow solid was dried on the filter under nitrogen for 3 d to provide the title compound (475 g, 1.175 mmol, 48% yield) as a beige/yellow solid. The mother liquor (about 8 L) was concentrated to about 2 L, whereupon solids began to crash out., The slurry was heated to 50° C., held for 2 h, cooled to 5° C. over 2 h, stirred overnight, and filtered. The cake was washed with MeTHF (100 mL) and dried overnight under vacuum at 40° C. to provide additional title compound (140 g, 0.346 mol, 14% yield).

A mixture of the total product of the previous step, combined with the product of a second batch at the same scale (1500 g, 3.710 mol) and MeTHF (4 L) was stirred at 20° C. for 2 h and filtered. The reactor and cake were washed with MeTHF (1.5 L). The resulting beige to yellow solid was dried under nitrogen for 3 d to provide the title compound as a beige yellow solid (1325 g, 3.184 mol, 86% yield (overall 68% yield), 97% purity). HPLC Method A Retention time 8.77 min Preparation 3: 5-benzyl-2-(6-bromo-1H-indazol-3-yl)-4,5,6,7-tetrahydro-1H-imidazo[4,5-c]pyridine

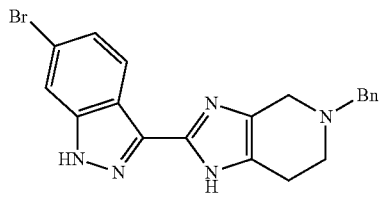 [SMILES: Brc1ccc2c(-c3nc4c([nH]3)CCN(Cc3ccccc3)C4)n[nH]c2c1]

To a 15 L flask was added 5-benzyl-2-(6-bromo-1H-indazol-3-yl)-5H-imidazo[4,5-c]pyridine (440 g, 1.088 mol) followed by MeTHF (4.5 L), methanol (2.25 L) and water (1.125 L). The slurry was cooled to 20° C., stirred for 1 h, and $NaBH_4$ (247 g, 6.530 mol) was added. The reaction mixture was stirred at 25° C. for 18 h. Water (1.125 L) was added followed by 20 wt %. sodium chloride solution (1.125 L) and the mixture was stirred for 30 min and the layers allowed to separate. The aqueous layer was drained. A premixed solution of NaOH (522 g) and water (5 L) was added and the reaction mixture was stirred for 60 min; the layers were allowed to separate and the aqueous layer was drained. Two additional batches at the same scale were prepared.

The organic layer from one batch was concentrated under reduced pressure in a 15 L jacketed reactor with the jacket set at 50° C., internal temperature 20° C. The additional batches were added to the reactor and concentrated one at a time resulting in a slurry about 6 L in volume. The slurry was heated to 50° C., IPAc (6 L) was added and the mixture was held at 60° C. for 1.5 h, cooled to 20° C. for 10 h, heated to 60° C. for 50 h, cooled to 20° C. in 5 h, then cooled to 5° C. and held for 3 h. The mixture was filtered and the reactor and cake was washed with a premixed solution of IPAc (1 L) and MeTHF (1 L), precooled to 5° C. The solids were dried under nitrogen on the filter at 40° C. for 3 d to provide the title compound (1059 g, 2.589 mol, 79% yield) as an off-white solid. The material was further dried in a vacuum oven at 50-60° C. for 8 h and at 27° C. for 2 d to provide the title compound (1043 g, 2.526 mol, 77% yield, 99% purity). HPLC Method A Retention time 6.73 min.

Preparation 4: (4-(Benzyloxy)-2-ethyl-5-fluorophenyl)trifluoroborate, potassium

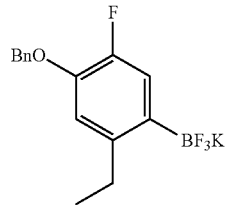

(a) 2-(4-(Benzyloxy)-2-ethyl-5-fluorophenyl)-4,4,5,5-tetramethyl-1,3,2-dioxaborolane A mixture of 1-(benzyloxy)-4-bromo-5-ethyl-2-fluorobenzene (520 g, 1682 mmol) and dioxane (5193 mL) was purged with nitrogen and then bis(pinacolato)diboron (641 g, 2523 mmol) was added followed by potassium acetate (495 g, 5046 mmol). The reaction mixture was purged with nitrogen; Pd(dppf)Cl$_2$ (41.2 g, 50.5 mmol) was added; the reaction mixture was purged with nitrogen, heated at 103° C. under nitrogen for 5 h; and cooled to RT. The reaction mixture was concentrated by vacuum distillation and partitioned between ethyl acetate (5204 mL) and water (5212 mL). The reaction mixture was filtered through Celite; the organic layer was washed with brine (2606 mL) followed by solvent removal by vacuum distillation to provide crude product as a thick black oil (-800 g).

The crude product was dissolved in DCM (1289 mL) and purified by silica gel chromatography (2627 g silica preslurried in hexane, eluted with 20% ethyl acetate in hexanes (10.35 L)). Solvent was removed by vacuum distillation to yield a light yellow oil (600 g). HPLC Method B Retention time 33.74 min.

(b) (4-(benzyloxy)-2-ethyl-5-fluorophenyl)trifluoroborate, potassium

The product of the previous step (200 g, 561 mmol) was mixed with acetone (1011 mL) until complete dissolution and methanol (999 mL) was added followed by 3 M potassium hydrogen difluoride (307 g, 3930 mmol) dissolved in water (1310 mL).

The reaction mixture was stirred for 3.5 h. Most of the organic solvent was removed by vacuum distillation. Water (759 mL) was added and the resulting thick slurry was stirred for 30 min and filtered. The cake was washed with water (506 mL) and the solids were dried on the filter for 30 min. The solids were slurried in acetone (1237 mL) and stirred for 1 h. The resulting slurry was filtered and the solids washed with acetone (247 mL).

The acetone solution was concentrated by vacuum distillation, and a constant volume (2 L) was maintained by slow addition of toluene (2983 mL) until all acetone and water had been distilled. The toluene solution was distilled to a thick yellow slurry by rotary evaporation, during which time the products precipitated as white solids. An additional portion of toluene (477 mL) was added to the mixture and stirred for 1 h. The mixture was then filtered and rinsed with toluene (179 mL) and dried under vacuum at 50° C. for 24 h to provide the title compound (104 g, 310 mmol, 55% yield) as a free-flowing, fluffy, slightly off-white solid. HPLC Method B Retention time 27.71 min.

Preparation 5: 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine

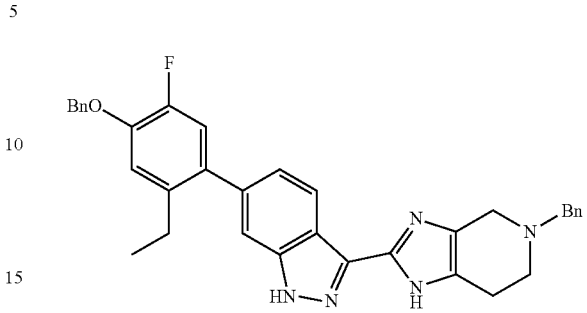

(a) 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine A mixture of bis(pinacolato)diboron (250 g, 984 mmol) and IPA (1.88 L) was stirred to dissolution and then a solution of potassium hydrogen difluoride (538 g, 6.891 mol) in water (2.31 L) was added portion-wise over 10 min. The reaction mixture was stirred for 1 h and filtered. The gel-like solids were slurried with water (1.33 L) until the mixture formed a clear hydrogel and then for another 45 min. The resulting solids/gel were filtered, then reslurried in acetone (1.08 L), filtered, air dried on the filter for 30 min and dried overnight to provide a fluffy white solid (196.7 g).

To a 5 L flask was added 5-benzyl-2-(6-bromo-1H-indazol-3-yl)-4,5,6,7-tetrahydro-1H-imidazo[4,5-c]pyridine (135 g, 331 mmol), (4-(benzyloxy)-2-ethyl-5-fluorophenyl)-trifluoroborate, potassium (133 g, 397 mmol), and the white solid product of the previous step (40.5 g) followed by MeTHF (1.23 L) and MeOH (1.75 L). The resulting slurry was degassed three times with nitrogen. To the slurry was added a degassed solution of cesium carbonate (431 g, 1.323 mol) in water (1.35 L). The slurry was degassed twice, Pd (amphos)2C12 (11.71 g, 16.53 mmol) was added, the slurry was again degassed twice and the reaction mixture was stirred at 67° C. overnight and cooled to 20° C. The layers were separated and back extracted with MeTHF (550 mL). The organic layers were combined and concentrated by rotary evaporation until solids precipitated. MeTHF (700 mL) was added and the reaction mixture was stirred at 65° C. The layers were separated and the aqueous phase back extracted with MeTHF (135 mL). The organic phases were combined and concentrated to about 300 mL resulting in a thick orange slurry. To the slurry was added MeOH (270 mL) followed by 1M HCl (1.325 L) at 20° C. with rapid stirring. The reaction mixture was stirred for 5 min and water (1 L) was added and the resulting slurry was stirred for 1 h. The solids were filtered, washed with water (150 mL), dried on the filter for 10 min and at 45° C. under nitrogen for 16 h to provide the 2 HCl salt of the title compound (221.1 g, 351 mmol, 92.2% purity) as a light yellow solid. HPLC Method B retention time 23.41 min.

Preparation 6: 5-ethyl-2-fluoro-4-(3-(4,5,6,7-tetrahydro-1H-imidazo[4,5-c]pyridin-2-yl)-1H-indazol-6-yl)phenol

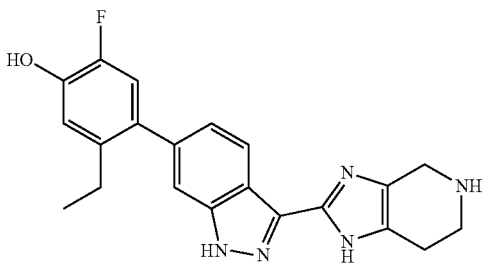 [SMILES: CCc1cc(O)c(F)cc1-c1ccc2c(-c3nc4c([nH]3)CCNC4)n[nH]c2c1]

To a 1 L flask was added 5-benzyl-2-(6-(4-(benzyloxy)-2-ethyl-5-fluorophenyl)-1H-indazol-3-yl)-4,5,6,7-tetrahydro-1H-imidazo[4,5-c]pyridine, 2 HCl (40 g, 63.4 mmol) as a slurry in ethanol (348 mL) and 1.25 M HCl in MeOH (101 mL) and water (17.14 mL). The reaction mixture was degassed with nitrogen for 5 min and 10 wt % Pd/C, 50 wt % $H_2O$ (4.05 g, 1.903 mmol) was added. The reactor was sealed, purged with $H_2$ pressurized to 1-2 psi. warmed to 50° C., and the reaction mixture was stirred overnight and filtered through Celite. The reactor and filter were washed with methanol (100 mL).

The filtered solution was combined with the product of a second batch at the 98 mmol scale and concentrated to 390 g. EtOAc (2.04 L) was added slowly with stirring and then the solution was cooled to 5° C. with stirring. Solids were filtered, washed with EtOAc (510 mL), and dried overnight at 45° C. under nitrogen to provide the 2 HCl salt of the title compound (58 g, 80% yield) as an off-white solid. HPLC Method B retention time 12.83 min.

Example 1

5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol Hydrate

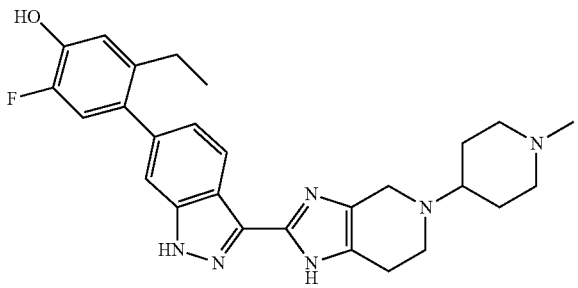 [SMILES: CCc1cc(O)c(F)cc1-c1ccc2c(-c3nc4c([nH]3)CCN(C3CCN(C)CC3)C4)n[nH]c2c1]

To a 125 mL flask was added NMP (19.23 mL) and 5-ethyl-2-fluoro-4-(3-(4,5,6,7-tetrahydro-1H-imidazo[4,5-c]pyridin-2-yl)-1H-indazol-6-yl)phenol, 2 HCl (6 g, 13.32 mmol) with stirring followed by NMP (19.23 mL). Acetic acid (2.52 mL) was added and then 1-methylpiperidin-4-one (3.28 mL, 26.6 mmol) was added in a single portion and the reaction mixture was stirred at 25° C. for 30 min and cooled to 15° C. Sodium triacetoxyborohydride (7.91 g, 37.3 mmol) was added and the external jacket was set to 20° C. after 20 min. After 3.5 h, total solution volume was 35 mL. The reactor was washed with methanol (5 mL). Half the solution (17.5 mL) followed by half the methanol wash (2.5 mL) was added to a premixed solution of methanol (28 mL), ammonium hydroxide (17 mL, 270 mmol) and water (9 mL) maintaining the temperature below 5° C. Solids precipitated after 10 min. The slurry was stirred for 30 min, ACN (60 mL) was added slowly over 30 min and the slurry was stirred for 2 h at 0° C., filtered and rinsed with ACN. The solids were dried at 50° C. for 12 h to provide the title compound (2.95 g, 93.2% yield, (85.2% yield, corrected for water content)) as an off-white solid. HPLC Method C retention time 12.11 min Example 2

Crystalline Hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol To a solution of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (10 g, 21.07 mmol), prepared as in Example A, in DMSO (19.99 mL) was added ethanol (19.93 mL). Undissolved solids were removed by filtration and half the DMSO solution was added to a stirred solution of 20% water in methanol (30 mL). A slurry formed after 10 min, which was stirred at RT for 4 h and filtered. The resulting yellow solids were dried for 3 h at 50° C. under nitrogen. The solids were slurried in 20% water in acetone (110 mL) at 45° C. with stirring for 35 h, filtered, and washed with 15% water in acetone and dried overnight to provide the title compound (4.40 g, 88% yield) as a light yellow solid.

Example 3

Crystalline Oxalate Hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol In a 20-mL glass vial, Compound 1 crystalline hydrate (248.5 mg), the product of Example 2, and oxalic acid anhydrate (48.0 mg) were dissolved in 1:1 tetrahydrofuran:water (5 mL). Acetonitrile (5 mL) was added producing a suspension. The resulting reaction mixture was stirred for one day at RT, filtered, washed with acetonitrile (2 mL), and dried under ambient conditions overnight to provide the title compound.

Example 4

Crystalline Succinate Hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol In a 4-mL glass vial, Compound 1 crystalline hydrate (40 mg) and succinic acid (10 mg) were suspended in isopropanol (1 mL). The reaction mixture suspension was stirred for seven days at RT. The solids were filtered, washed with isopropanol (0.5 mL), and dried under ambient conditions overnight to provide a crystalline succinate solvate. The isolated succinate solvate solid was dried at 150° C. for 30 min under vacuum oven to provide a second solid form, which was equilibrated at 80% to 90% relative humidity for one day at RT to provide the title compound.

Examples 5-7

Properties of the Solid Forms of the Invention

Samples of the crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol of Example 3 and the crystalline hydrate of the succinate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol of Example 4 were analyzed by powder X-ray diffraction (PXRD), differential scanning calorimetry (DSC), thermogravimetric analysis (TGA), and dynamic moisture sorption (DMS).

Example 5

Powder X-Ray Diffraction

The powder X-ray diffraction patterns of FIG. 1 was obtained with a Bruker D8-Advance X-ray diffractometer using Cu-Kα radiation (λ=1.54054 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 40° in 2θ with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within±0.02° two-theta angle. Observed PXRD 2θ peak positions and d-spacings are shown in Tables 1 and 2 for the crystalline oxalate hydrate and crystalline succinate hydrate of the invention, respectively.

TABLE 1

PXRD Data for the Crystalline Oxalate Hydrate

| 2θ | d(Å) | Area | A % |
| --- | --- | --- | --- |
| 6.77 | 13.05 | 31716 | 41.0 |
| 11.56 | 7.65 | 6303.00 | 8.20 |
| 12.13 | 7.29 | 20994 | 27.2 |
| 13.54 | 6.53 | 77308 | 100.0 |
| 14.29 | 6.19 | 4903.00 | 6.30 |
| 16.96 | 5.22 | 9024 | 11.7 |
| 17.23 | 5.14 | 27774 | 35.9 |
| 17.72 | 5.00 | 19582 | 25.3 |
| 18.00 | 4.92 | 39472 | 51.1 |
| 18.55 | 4.78 | 31259 | 40.4 |
| 18.76 | 4.73 | 18293 | 23.7 |
| 19.51 | 4.55 | 14796 | 19.1 |
| 20.18 | 4.40 | 11319 | 14.6 |
| 20.69 | 4.29 | 16629 | 21.5 |
| 21.38 | 4.15 | 14261 | 18.4 |
| 21.98 | 4.04 | 18621 | 24.1 |
| 22.30 | 3.98 | 17504 | 22.6 |
| 23.63 | 3.76 | 14213 | 18.4 |
| 24.12 | 3.69 | 29375 | 38.0 |
| 24.34 | 3.65 | 19430 | 25.1 |
| 24.67 | 3.61 | 15460 | 20.0 |
| 27.05 | 3.29 | 20767 | 26.9 |
| 27.26 | 3.27 | 24154 | 31.2 |
| 28.85 | 3.09 | 8021 | 10.4 |
| 29.80 | 3.00 | 14992 | 19.4 |

TABLE 1-continued

PXRD Data for the Crystalline Oxalate Hydrate

| 2θ | d(Å) | Area | A % |
| --- | --- | --- | --- |
| 30.13 | 2.96 | 17939 | 23.2 |
| 31.05 | 2.88 | 7191 | 9.3 |

TABLE 2

PXRD Data for the Crystalline Succinate Hydrate

| 2θ | d(Å) | Area | A % |
| --- | --- | --- | --- |
| 4.81 | 18.34 | 58400 | 25.80 |
| 9.66 | 9.14 | 92725 | 41.00 |
| 10.46 | 8.45 | 17225 | 7.60 |
| 13.45 | 6.58 | 5912 | 2.60 |
| 13.78 | 6.42 | 6010 | 2.70 |
| 14.93 | 5.93 | 93135 | 41.20 |
| 16.21 | 5.46 | 24930 | 11.00 |
| 16.78 | 5.28 | 226066 | 100.00 |
| 17.45 | 5.08 | 49392 | 21.80 |
| 19.10 | 4.64 | 53460 | 23.60 |
| 19.61 | 4.52 | 80964 | 35.80 |
| 21.20 | 4.19 | 70129 | 31.00 |
| 21.92 | 4.05 | 51995 | 23.00 |
| 22.87 | 3.88 | 67007 | 29.60 |
| 24.77 | 3.59 | 81836 | 36.20 |
| 27.27 | 3.27 | 4553 | 2.00 |
| 28.09 | 3.17 | 18019 | 8.00 |
| 28.77 | 3.10 | 17372 | 7.70 |
| 30.68 | 2.91 | 5202 | 2.30 |
| 31.74 | 2.82 | 14150 | 6.30 |

Example 6

Thermal Analysis

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C/min from 0° C. to 250° C. A representative DSC thermogram of the crystalline oxalate hydrate and crystalline succinate hydrate of the invention is shown in FIGS. 2 and 6, respectively.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300° C. The balance and furnace chambers were purged with nitrogen flow during use. A representative TGA trace of the crystalline oxalate hydrate and crystalline succinate hydrate of the invention is shown in FIGS. 3 and 7, respectively.

Example 7

Dynamic Moisture Sorption Assessment

Dynamic moisture sorption (DMS) measurement was performed using a VTI atmospheric microbalance, SGA-100 system (VTI Corp., Hialeah, FL 33016). A weighed sample was used and the humidity was lowest possible value (close to 0% RH) at the start of the analysis. The DMS analysis consisted of an initial drying step (~0%RH) for 120 minutes, followed by two cycles of sorption and desorption with a scan rate of 5% RH/step over the humidity range of 5% RH to 90% RH. The DMS run was performed isothermally at 25° C. A representative DMS trace for the crystalline oxalate hydrate and crystalline succinate hydrate of the invention is shown in FIGS. 4 and 8, respectively.

Biological Assays 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (compound 1) has been characterized in the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

The serially diluted compound was pre-incubated with each of the four JAK enzymes and the substrate in white 384-well microplates (Corning) at ambient temperature for 1h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to $pK_1$ (negative logarithm of dissociation constant, Ki) using the Cheng-Prusoff equation.

Compound 1 exhibited the following enzyme potency.

TABLE 2

| JAK 1 $pK_i$ | JAK 2 $pK_i$ | JAK 3 $pK_i$ | Tyk2 $pK_i$ |
|---|---|---|---|
| 10.2 | 10.8 | 9.7 | 9.8 |

Assay 2: Cellular JAK Potency Assay: Inhibition of IL-13

The AlphaScreen JAM cellular potency assay was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% $CO_2$ humidified incubator in 50% DMEM/50% F-12 medium (Life Technologies) supplemented with 10% FBS (Hyclone), 100 U/mL penicillin, 100 μg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 μL medium, and were allowed to adhere overnight in the incubator. On day 2 of the assay, the medium was removed and replaced with 12 μL of assay buffer (Hank's Balanced Salt Solution/HBSS, 25 mM HEPES, and 1 mg/ml bovine serum albumin/BSA) containing dose-responses of test compounds. The compound was serially diluted in DMSO and then diluted another 1000-fold in media to bring the final DMSO concentration to 0.1%. Cells were incubated with test compounds at 37° C. for 1 h, and followed by the addition of 12 μl of pre-warmed IL-13 (80 ng/mL in assay buffer) for stimulation. After incubating at 37° C. for 30 min, the assay buffer (containing compound and IL-13) was removed, and 10 μL of cell lysis buffer (25 mM HEPES, 0.1% SDS, 1% NP-40, 5 mM $MgCl_2$, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and IC50 values were determined from a 4-parameter robust fit model with the Prism software. Results may also be expressed as the negative logarithm of the $IC_{50}$ value, $pIC_{50}$. Compound 1 exhibited a $pIC_{50}$ value of 8.2 in this assay.

Assay 3: Cellular JAK Potency Assay: Inhibition of IL-2/anti-CD3 Stimulated IFNγ in human PBMCs The potency of the test compound for inhibition of interleukin-2 (IL-2)/anti-CD3 stimulated interferon gamma (IFNy) was measured in human peripheral blood mononuclear cells (PBMCs) isolated from human whole blood (Stanford Blood Center). Because IL-2 signals through JAK, this assay provides a measure of JAK cellular potency.

(1) Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10%

Heat Inactivated Fetal Bovine Serum (FBS, Life Technologies), 2 mM Glutamax (Life Technologies), 25 mM HEPES (Life Technologies) and 1× Pen/Strep (Life Technologies). Cells were seeded at 200,000 cells/well in media (50 μL) and cultured for 1 h. Compounds were serially diluted in DMSO and then diluted another 500-fold (to a 2× final assay concentration) in media. Test compounds (100 μL/well) were added to cells, and incubated at 37° C., 5% $CO_2$ for 1 h, followed by the addition of IL-2 (R&D Systems; final concentration 100 ng/mL) and anti-CD3 (BD Biosciences; final concentration 1 μg/mL) in pre-warmed assay media (50 μL) for 24 h.

(2) After cytokine stimulation, cells were centrifuged at 500 g for 5 min and supernatants removed and frozen at −80° C. To determine the inhibitory potency of the test compound in response to IL-2/anti-CD3, supernatant IFNγ concentrations were measured via ELISA (R&D Systems). $IC_{50}$ values were determined from analysis of the inhibition curves of concentration of IFNy vs compound concentration. Data are expressed as $pIC_{50}$ (negative decadic logarithm $IC_{50}$) values. Compound 1 exhibited a $pIC_{50}$ value of about 7.3 in this assay.

Assay 4: Cellular JAK Potency Assay: Inhibition of IL-2 Stimulated pSTAT5 in CD4+T cells The potency of the test compound for inhibition of interleukin-2 (IL-2)/anti-CD3 stimulated STATS phosphorylation was measured in CD4-positive (CD4+) T cells in human peripheral blood mononuclear cells (PBMCs) isolated from human whole blood (Stanford Blood Center) using flow cytometry. Because IL-2 signals through JAK, this assay provides a measure of JAK cellular potency.

CD4+T cells were identified using a phycoerythrobilin (PE) conjugated anti-CD4 antibody (Clone RPA-T4, BD Biosciences), while an Alexa Fluor 647 conjugated anti-pSTAT5 antibody (pY694, Clone 47, BD Biosciences) was used to detect STATS phosphorylation.

(1) The protocol of Assay 3 paragraph (1) was followed with the exception that the cytokine stimulation with anti-CD3 was performed for 30 min instead of 24 h. (2) After cytokine stimulation, cells were fixed with pre warmed fix solution (200 4; BD Biosciences) for 10 min at 37° C., 5% $CO_2$, washed twice with DPBS buffer (1 mL, Life Technologies), and resuspended in ice cold Perm Buffer III (1000 4, BD Biosciences) for 30 min at 4° C. Cells were washed twice with 2% FBS in DPBS (FACS buffer), and then resuspended in FACS buffer (100 4) containing anti-CD4 PE (1:50 dilution) and anti-CD3 anti-CD3Alexa Fluor 647 (1:5 dilution) for 60 min at room temperature in the dark. After incubation, cells were washed twice in FACS buffer before being analyzed using a LSRII flow cytometer (BD Biosciences). To determine the inhibitory potency of the test compound in response to IL-2/anti-CD3, the median fluorescent intensity (MFI) of pSTAT5 was measured in CD4+ T cells. $IC_{50}$ values were determined from analysis of the inhibition curves of MFI vs compound concentration. Data are expressed as $pIC_{50}$ (negative decadic logarithm IC50) values. Compound 1 exhibited a $pIC_{50}$ value of about 7.7 in this assay.

Assay 5: Cellular JAK Potency Assay: Inhibition of IL-4 Stimulated pSTAT6 in CD3+ T cells The potency of the test compound for inhibition of interleukin-4 (IL-4) stimulated STAT6 phosphorylation was measured in CD3-positive (CD3+) T cells in human peripheral blood mononuclear cells (PBMCs) isolated from human whole blood (Stanford Blood Center) using flow cytometry. Because IL-4 signals through JAK, this assay provides a measure of JAK cellular potency.

CD3+ T cells were identified using a phycoerythrobilin (PE) conjugated anti-CD3 antibody (Clone UCHT1, BD Biosciences), while an Alexa Fluor 647 conjugated anti-pSTAT6 antibody (pY641, Clone 18/P, BD Biosciences) was used to detect STAT6 phosphorylation.

Human peripheral blood mononuclear cells (PBMC) were isolated from human whole blood of healthy donors as in Assays 3 and 4. Cells were seeded at 250,000 cells/well in media (200 4), cultured for 1 h and then resuspended in assay media (50 μL) (RPMI supplemented with 0.1% bovine serum albumin (Sigma), 2 mM Glutamax, 25 mM HEPES and 1× Penstrep) containing various concentrations of test compounds. Compounds were serially diluted in DMSO and then diluted another 500-fold (to a 2× final assay concentration) in assay media. Test compounds (50 μL) were incubated with cells at 37° C., 5% $CO_2$ for 1 h, followed by the addition of IL-4 (50 μL) (R&D Systems; final concentration 20 ng/mL) in pre-warmed assay media for 30 min. After cytokine stimulation, cells were fixed with pre-warmed fix solution (100 μL) (BD Biosciences) for 10 min at 37° C., 5% $CO_2$, washed twice with FACS buffer (1 mL) (2% FBS in DPBS), and resuspended in ice cold Perm Buffer III (1000 μL) (BD Biosciences) for 30 min at 4° C. Cells were washed twice with FACS buffer, and then resuspended in FACS buffer (100 μL) containing anti-CD3 PE (1:50 dilution) and anti-pSTAT6 Alexa Fluor 647 (1:5 dilution) for 60 min at room temperature in the dark. After incubation, cells were washed twice in FACS buffer before being analyzed using a LSRII flow cytometer (BD Biosciences).

To determine the inhibitory potency of the test compound in response to IL-4, the median fluorescent intensity (MFI) of pSTAT6 was measured in CD3+ T cells. $IC_{50}$ values were determined from analysis of the inhibition curves of MFI vs compound concentration. Data are expressed as $pIC_{50}$ (negative decadic logarithm $IC_{50}$). Compound 1 exhibited a $pIC_{50}$ value of 8.1 in this assay.

Assay 6: Cellular JAK Potency Assay: Inhibition of IL-6 Stimulated pSTAT3 in CD3+ T cells A protocol analogous to that of Assay 5 was used to determine the potency of the test compound for inhibition of interleuken-6 (IL-6) stimulated STAT3 phosphorylation.

An Alexa Fluor 647 conjugated anti-pSTAT3 antibody (pY705, Clone 4/P, BD Biosciences) was used to detect STAT3 phosphorylation.

Compound 1 exhibited a $pIC_{50}$ value of 7.4 in this assay.

Assay 7: Cellular JAK Potency Assay: Inhibition of IFNγ-Induced pSTAT1

The potency of the test compound for inhibition of interferon gamma (IFNγ) stimulated STAT1 phosphorylation was measured in CD14-positive (CD14+) monocytes derived from human whole blood (Stanford Blood Center) using flow cytometry. Because IFNγ signals through JAK, this assay provides a measure of JAK cellular potency.

Monocytes were identified using a fluorescein isothiocyanate (FITC) conjugated anti-CD14 antibody (Clone RM052, Beckman Coulter), and an Alexa Fluor 647 conjugated anti-pSTAT1 antibody (pY701, Clone 4a, BD Biosciences) was used to detect STAT1 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Fetal Bovine Serum (FBS, Life Technologies), 2 mM Glutamax (Life Technologies), 25 mM HEPES (Life Technologies) and 1× Pen/Strep (Life Technologies). Cells were seeded at 250,000 cells/well in media (200 4), cultured for 2 h and resuspended in assay media (50 4) (RPMI supplemented with 0.1% bovine serum albumin (Sigma), 2 mM Glutamax, 25 mM HEPES and 1X Penstrep) containing various concentrations of test compounds. The compound was serially diluted in DMSO and then diluted another 1000-fold in media to bring the final DMSO concentration to 0.1%. Test compound dilutions were incubated with cells at 37° C., 5% $CO_2$ for 1 h, followed by the addition of pre-warmed IFNγ (R&D Systems) in media (50 4) at a final concentration of 0.6 ng/mL for 30 min. After cytokine stimulation, cells were fixed with pre-warmed fix solution (100 μL) (BD Biosciences) for 10 min at 37° C., 5% $CO_2$, washed twice with FACS buffer (1 mL) (1% BSA in PBS), resuspended in 1:10 anti-CD14 FITC:FACS buffer (100 μL), and incubated at 4° C. for 15 min. Cells were washed once, and then resuspended in ice cold Perm Buffer III (BD Biosciences) (100 μL) for 30 min at 4° C. Cells were washed twice with FACS buffer, and then resuspended in 1:10 anti-pSTAT1 Alexa Fluor 647:FACS buffer (100 μL) for 30 min at RT in the dark, washed twice in FACS buffer, and analyzed using a LSRII flow cytometer (BD Biosciences).

To determine the inhibitory potency of the test compound, the median fluorescent intensity (MFI) of pSTAT1 was measured in CD14+ monocytes. $IC_{50}$ values were determined from analysis of the inhibition curves of MFI vs compound concentration. Data are expressed as $pIC_{50}$ (negative decadic logarithm $IC_{50}$) values. Compound 1 exhibited a $pIC_{50}$ value of about 7.5 in this assay.

Assay 8: Pharmacokinetics in Plasma and Lung in Mouse

Plasma and lung levels of test compounds and ratios thereof were determined in the following manner. BALB/c mice from Charles River Laboratories were used in the assay. Test compounds were individually formulated in 20% propylene glycol in pH 4 citrate buffer at a concentration of 0.2 mg/mL and 50 uL of the dosing solution was introduced into the trachea of a mouse by oral aspiration. At various time points (typically 0.167, 2, 6, 24 hr) post dosing, blood samples were removed via cardiac puncture and intact lungs were excised from the mice. Blood samples were centrifuged (Eppendorf centrifuge, 5804R) for 4 minutes at approximately 12,000 rpm at 4° C. to collect plasma. Lungs were padded dry, weighed, and homogenized at a dilution of 1:3 in sterile water. Plasma and lung levels of test compound were determined by LC-MS analysis against analytical standards constructed into a standard curve in the test matrix. A lung to plasma ratio was determined as the ratio of the lung AUC in μg hr/g to the plasma AUC in μg hr/mL, where AUC is conventionally defined as the area under the curve of test compound concentration vs. time.

Compound 1 exhibited exposure in lung about 55 times greater than exposure in plasma in mouse.

Assay 9: Murine (Mouse) model of IL-13 induced pSTAT6 induction in lung tissue 11-13 is an important cytokine underlying the pathophysiology of asthma (Kudlacz et al. *Eur. J. Pharmacol,* 2008, 582,154-161). IL-13 binds to cell surface receptors activating members of the Janus family of kinases (JAK) which then phosphorylate STAT6 and subsequently activates further transcription pathways. In the described model, a dose of IL-13 was delivered locally into the lungs of mice to induce the phosphorylation of STAT6 (pSTAT6) which is then measured as the endpoint.

Adult balb/c mice from Harlan were used in the assay. On the day of study, animals were lightly anesthetized with isoflurane and administered either vehicle or test compound (0.5 mg/mL, 50 μL total volume over several breaths) via oral aspiration. Animals were placed in lateral recumbency post dose and monitored for full recovery from anesthesia before being returned to their home cage. Four hours later, animals were once again briefly anesthetized and challenged with either vehicle or IL-13 (0.03 μg total dose delivered, 50 μL total volume) via oral aspiration before being monitored for recovery from anesthesia and returned to their home cage. One hour after vehicle or IL-13 administration, lungs were collected for both pSTAT6 detection using an anti-pSTAT6 ELISA (rabbit mAb capture/coating antibody; mouse mAb detection/report antibody: anti-pSTAT6-pY641; secondary antibody: anti-mouse IgG-HRP) and analyzed for total drug concentration as described above in Assay 12.

Activity in the model is evidenced by a decrease in the level of pSTAT6 present in the lungs of treated animals at 5 hours compared to the vehicle treated, IL-13 challenged control animals. The difference between the control animals which were vehicle- treated, IL-13 challenged and the control animals which were vehicle-treated, vehicle challenged dictated the 0% and 100% inhibitory effect, respectively, in any given experiment. Compound 1 exhibited about 60% inhibition of STAT6 phosphorylation at 4 hours after IL-13 challenge.

Assay 10: Murine model of *Alternaria alternata*-induced eosinophilic inflammation of the lung Airway eosinophilia is a hallmark of human asthma. *Alternaria alternata* is a fungal aeroallergen that can exacerbate asthma in humans and induces eosinophilic inflammation in the lungs of mice (Havaux et al. *Clin Exp Immunol.* 2005, 139(2):179-88). In mice, it has been demonstrated that alternaria indirectly activates tissue resident type 2 innate lymphoid cells in the lung, which respond to (e.g. IL-2 and IL-7) and release JAK-dependent cytokines (e.g. IL-5 and IL-13) and coordinate eosinophilic inflammation (Bartemes et al. *J Immunol.* 2012, 188(3):1503-13).

Seven- to nine-week old male C57 mice from Taconic were used in the study. On the day of study, animals were lightly anesthetized with isoflurane and administered either vehicle or test compound (0.1-1.0 mg/mL, 50 μL total volume over several breaths) via oropharyngeal aspiration. Animals were placed in lateral recumbency post dose and monitored for full recovery from anesthesia before being returned to their home cage. One hour later, animals were once again briefly anesthetized and challenged with either vehicle or alternaria extract (200 ug total extract delivered, 50 μL total volume) via oropharyngeal aspiration before being monitored for recovery from anesthesia and returned to their home cage. Forty-eight hours after alternaria administration, bronchoalveolar lavage fluid (BALF) was collected and eosinophils were counted in the BALF using the Advia 120 Hematology System (Siemens).

Activity in the model is evidenced by a decrease in the level of eosinophils present in the BALF of treated animals at forty-eight hours compared to the vehicle treated, alternaria challenged control animals. Data are expressed as percent inhibition of the vehicle treated, alternaria challenged BALF eosinophils response. To calculate percent inhibition, the number of BALF eosinophils for each condition is converted to percent of the average vehicle treated, alternaria challenged BALF eosinophils and subtracted from one-hundred percent. Compound 1 exhibited about 88% inhibition of BALF eosinophil counts at forty-eight hours after alternaria challenge.

Assay 11: Murine model of LPS/G-CSF/IL-6/IFNγ Cocktail-Induced Airway Neutrophilic Inflammation of the Lung Model Airway neutrophilia is a hallmark of a range of respiratory disease in humans. Compound 1 was tested in a model of neutrophilic airway inflammation using a LPS/G-CSF/IL-6/IFNγ cocktail to induce airway neutrophilia.

Seven- to nine-week old male Balb/C (wildtype) mice from Jackson Laboratory were used in the study. On the day of study, animals were lightly anesthetized with isoflurane and administered either vehicle or test compound (1.0 mg/mL, 50 μL total volume over several breaths) via oropharyngeal aspiration. Animals were placed in lateral recumbency post dose and monitored for full recovery from anesthesia before being returned to their home cage. One hour later, animals were once again briefly anesthetized and challenged with either vehicle or LPS; 0.01 mg/kg/G-CSF;

5 μg/IL-6; 5 μg/IFNγ; 5 μg (100 μL total volume) via oropharyngeal aspiration (OA). Twenty-four hours after the LPS/G-CSF/IL-6/IFNg cocktail administration, bronchoalveolar lavage fluid (BALF) was collected and neutrophils were counted.

Upon OA treatment with compound 1, there was a statistically significant reduction of the airway neutrophils (84% compared to vehicle treated mice), demonstrating that the blockade of JAK-dependent signaling has effects on neutrophilic airway inflammation.

Assay 12: Ocular Pharmacokinetics in Rabbit Eyes

The objective of this assay was to determine the pharmacokinetics of the compound 1 in rabbit ocular tissues.

Solution Formulation

The compound of the invention, 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1) was dissolved in either 10% 2-hydroxypropyl-β-cyclodextrin to attain a target concentration of 4 mg/mL or in purified water to attain a target concentration of 1 mg/mL . Bilateral intravitreal injection (50 μL/eye) of the solution of test compound was administered to New Zealand white rabbits in two dose groups, 200 μg/eye and 50 μg/eye, respectively, for the cyclodextrin and water vehicle formulations, respectively. The test compound concentration was measured in ocular tissues: vitreous, aqueous, retina/choroid and iris-ciliary body at pre-determined time points post injection (30 min, 4 h, 1 d, 3 d, 7 d, 14 d). Two rabbits (four eyes) were dosed for each time point. In the vitreous tissue, compound 1 exhibited a two-phase decrease in concentration characterized by an initial decrease in concentration with a half-life of approximately 12 hours and finally a terminal half-life of approximately 3.6 days. The compound was found to distribute quickly into the retinal and choroidal region as well and shows a similar pharmacokinetic profile as in the vitreous tissue.

Suspension Formulation

A suspension formulation was prepared by combining crystalline compound 1 of Example 2 with 0.5% hydroxypropyl methylcellulose (HPMC E5)+0.02% Tween 80 to attain a target concentration of 10 mg/mL. Bilateral intravitreal injection (50 μL/eye) of the suspension of test compound was administered to New Zealand white rabbits (500 μg/eye). The test compound concentration was measured in ocular tissues as in the suspension formulation assay at 30 min, 2 wks, 4 wks, 6 wks, and 8 wks post injection. The compound showed a linear decrease in drug concentration in the vitreous from 30 min to 6 weeks with a clearance rate of approximately 3 μg/mL/day. The behavior is consistent with the solubility of compound 1 in the vehicle and the ocular pharmacokinetic behavior in the solution formulation. The drug concentration in plasma was measured and found to be at least 3 orders of magnitude lower than the concentration in vitreous tissue.

Assay 13: Pharmacodynamic Assay: Inhibition of IL6-induced pSTAT3 in Rats

The ability of a single intravitreal administration of test compound to inhibit IL-6 induced pSTAT3 was measured in rat retina/choroid homogenates.

Suspension formulations were prepared by combining crystalline compound 1 of Example 2 with 0.5% hydroxypropyl methylcellulose (HPMC E5 LV), 0.02% Tween 80, and 0.9% sodium chloride in purified water to attain target concentrations of 3 mg/mL and 10 mg/mL.

Female Lewis rats were intravitreally (IVT) dosed (5 μL per eye) with the suspension formulations or with the drug vehicle. Three days later, IL-6 (Peprotech; 0.1 mg/mL; 5 μL per eye) or vehicle was intravitreally administered to induce pSTAT3.

Ocular tissues were dissected one hour after the second IVT injection with IL-6. The retina/choroid tissues were homogenized and pSTAT3 levels were measured using an ELISA (Cell Signaling Technology). The percent inhibition of IL-6-induced pSTAT3 was calculated in comparison to the vehicle/vehicle and vehicle/IL-6 groups. Inhibition of greater than 100% reflects a reduction of pSTAT3 levels to below those observed in the vehicle/vehicle group.

With a 3 day pre-treatment prior to IL-6 challenge, the 15 μg dose and the 50 μg dose of the compound of the invention administered by the suspension formulation inhibited IL-6-induced pSTAT3 by 33% and 109%, respectively in the retina/choroid tissues.

Assay 14: Pharmacodynamic Assay: Inhibition of IFNγ-induced IP-10 in Rabbits

The ability of a single intravitreal administration of test compound to inhibit interferon-gamma (IFNγ) induced IP-10 protein levels was measured in rabbit vitreous and retina/choroid tissues.

Solution formulations at concentrations of 1 mg/mL and 4 mg/mL of compound 1 of Example 2 were prepared as in Assay 12. A suspension formulation was prepared by combining crystalline compound 1 of Example 2 with 0.5% hydroxypropyl methylcellulose (HPMC E5), 0.02% Tween 80, and 9 mg/mL sodium chloride in purified water to attain a target concentration of 20 mg/mL.

Male, New Zealand White rabbits (Liveon Biolabs, India) were used for the studies. Animals were acclimated after arrival at the research facilities (Jubilant Biosys Ltd., India). Each rabbit was given a total of two intravitreal (IVT) injections with a total dose volume of 50 μL per eye. The first IVT injection (45 μL per eye) delivered test compound or vehicle at a prescribed time point (i.e. 24 hours for the solution formulations or 1 week for the suspension formulation). The second IVT injection (5 μL per eye) delivered IFNγ (1 μg/eye; Stock solution 1 mg/mL; Kingfisher Biotech) or vehicle for the induction of IP-10. In brief, on the day of the injections, rabbits were anesthetized with an intramuscular injection of ketamine (35 mg/kg) and xylazine (5 mg/kg). Once deeply anesthetized, each eye was rinsed with sterile saline and IVT injections were performed using a 0.5 mL insulin syringe (50 units=0.5 mL) with a 31-gauge needle at the supra-nasal side of the both eyes by marking the position with a Braunstein fixed caliper (2 ¾") 3.5 mm from the rectus muscle and 4 mm from the limbus.

Tissues were collected 24 hours after the second IVT injection with IFNγ. Vitreous humor (VH) and retina/choroid tissues (R/C) were collected and homogenized, and IP-10 protein levels were measured using a rabbit CXCL10 (IP-10) ELISA kit (Kingfisher Biotech). The percent inhibition of IFNγ-induced IP-10 was calculated in comparison to the vehicle/vehicle and vehicle/IFNγ groups.

When dosed as a solution, with a 24 hour pre-treatment prior to the IFNγ challenge, 45 μg of compound 1 inhibited IFNγ-induced IP-10 by 70% and 86% in the vitreous humor and retina/choroid tissue, respectively, while 180 μg of the compound inhibited IFNγ-induced IP-10 by 91% and 100% in the vitreous humor and retina/choroid tissue, respectively.

With a 1 week pre-treatment prior to the IFNγ challenge, the crystalline suspension formulation of compound 1 inhibited IFNγ-induced IP-10 by 100% in both the vitreous humor and retina/choroid tissues.

Assay 15: Inhibition of IFNγ and IL-27 induced chemokines CXCL9 and CXCL10 in human 3D airway cultures EpiAirway tissue cultures were obtained from Mattek (AIR-100). Cultures were derived from asthmatic donors. In a cell culture insert, human derived tracheal/bronchial epithelial cells were grown and differentiated on a porous membrane support, allowing an air-liquid interface with warmed culture medium below the cells and a gaseous test atmosphere above. Tissues were cultured in maintenance media (Mattek, AIR-100-MM) in a 37° C., 5% CO2 humidified incubator. Four donors were tested. On Day 0, tissue cultures were treated with test compounds at 10 µM, 1 µM and/or 0.1 µM. Compounds were diluted in dimethyl sulfoxide (DMSO, Sigma) to a final concentration of 0.1%. DMSO at 0.1% was used as a vehicle control. Test compounds were incubated with cultures for 1 hour at 37° C., 5% $CO_2$, followed by the addition of pre-warmed media containing IFNγ (R&D Systems) or IL-27 (R&D Systems) at a final concentration at 100 ng/ml. Tissue cultures were maintained for 8 days. Media was replaced every 2 days with fresh media containing compounds and IFNγ or IL-27. On Day 8, tissue cultures and supernatants were collected for analysis. Supernatant samples were assayed for CXCL10 (IP-10) and CXCL9 (MIG) using luminex analysis (EMD Millipore). Data is expressed as % Inhibition +/−standard deviation (±STDV). Percent inhibition was determined by compound inhibitory potency against IFNγ or IL-27 induced CXCL10 or CXCL9 secretion compared to vehicle treated cells. Data is the average from 3 or 4 donors. Compound 1 was able to inhibit IFNγ induced CXCL10 secretion by 99%±2.0 (at 10 µM), 71%±19 (at µM) and 17%±12 (at 0.1 µM) when compared to vehicle control. Compound 1 was able to inhibit IFNγ induced CXCL9 secretion by 100%±0.3 (at 10 µM), 99%±0.9 (at 1 µM) and 74%±17 (at 0.1 µM) when compared to vehicle. Compound 1 was able to inhibit IL-27 induced CXCL10 secretion by 108%±11 (at 10 µM), 98%±10 (at 1 µM) and 73%±8.5 (at 0.1 µM) when compared to vehicle control. Compound 1 was able to inhibit IL-27 induced CXCL9 secretion by 100%±0 (at 10 µM), 95%±3.7 (at 1 µM) and 75%±3.5 (at 0.1 µM) when compared to vehicle control.

Assay 16: IL-5 Mediated Eosinophil Survival Assay

The potency of the test compound for IL-5 mediated eosinophil survival was measured in human eosinophils isolated from human whole blood (AllCells). Because IL-5 signals through JAK, this assay provides a measure of JAK cellular potency. Human eosinophils were isolated from fresh human whole blood (AllCells) of healthy donors. Blood was mixed with 4.5% Dextran (Sigma-Aldrich) in a 0.9% sodium chloride solution (Sigma-Aldrich). Red blood cells were left to sediment for 35 minutes. The leukocyte rich upper layer was removed and layered over Ficoll-Paque (GE Healthcare) and centrifuged at 600 g for 30 minutes. The plasma and mononuclear cell layers were removed before the granulocyte layer was lysed with water to remove any contaminating red blood cells. Eosinophils were further purified using a human eosinophil isolation kit (Miltenyi Biotec). A fraction of the purified eosinophils were incubated with anti-CD16 FITC (Miltenyi Biotec) for 10 minutes at 4° C. in the dark. Purity was analyzed using a LSRII flow cytometer (BD Biosciences).

Cells were cultured in a 37° C., 5% $CO_2$ humidified incubator in RPMI 1640 (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells were seeded at 10,000 cells/well in media (50 µL). The plate was centrifuged at 300 g for 5 minutes and supernatants removed. Compounds were serially diluted in DMSO and then diluted another 500-fold to a 2× final assay concentration in media. Test compounds (50 µL/well) were added to cells, and incubated at 37° C., 5% $CO_2$ for 1 hour, followed by the addition of IL-5 (R&D Systems; final concentrations 1 ng/mL and 10 pg/ml) in pre-warmed assay media (50 µL) for 72 hours.

After cytokine stimulation, cells were centrifuged at 300 g for 5 min and washed twice with cold DPBS (Life Technologies). To access viability and apoptosis, cells were incubated with Propidium Iodide (Thermo Fisher Scientific) and APC Annexin V (BD Biosciences) and analyzed using a LSRII flow cytometer (BD Biosciences). $IC_{50}$ values were determined from analysis of the viability curves of percent cell viability vs compound concentration. Data are expressed as $pIC_{50}$ (negative decadic logarithm $IC_{50}$) values. Compound 1 exhibited a $pIC_{50}$ value of 7.9±0.5 in the presence of 10 pg/ml IL-5 and a $pIC_{50}$ value of 6.5±0.2 in the presence of 1 ng/ml IL-5.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol.

2. The crystalline oxalate hydrate of claim 1, wherein the crystalline oxalate hydrate is characterized by a powder X-ray diffraction pattern comprising diffraction peaks at 2θ values of 6.77±0.20, 12.13±0.20, 13.54±0.20, 17.23±0.20, and 18.00±0.20.

3. The crystalline oxalate hydrate of claim 2 wherein the powder X-ray diffraction pattern is further characterized by having two or more additional diffraction peaks at 2θ values selected from 11.56±0.20, 14.29±0.20, 19.51±0.20, 21.38±0.20, and 23.63±0.20.

4. The crystalline oxalate hydrate of claim 1, wherein the crystalline oxalate hydrate is characterized by a powder X-ray diffraction pattern in which the peak positions are substantially in accordance with the peak positions of the pattern shown in FIG. 1.

5. The crystalline oxalate hydrate of claim 1 wherein the crystalline oxalate hydrate is characterized by a differential scanning calorimetry trace recorded at a heating rate of 10° C. per minute which shows a maximum in endothermic heat flow at a temperature between 266° C. and 276° C.

6. The crystalline oxalate hydrate of claim 1, wherein the crystalline oxalate hydrate is characterized by a differential scanning calorimetry trace substantially in accordance with that shown in FIG. 2.

7. A crystalline hydrate of the succinate salt of 5-ethyl-2-fluoro-4-(3-(5-(1-methylpiperidin-4-yl)-4,5,6,7-tetra-hydro-1H-imidazo[4,5-c]pyridin-2-yl)-1H-indazol-6-yl) phenol.

8. The crystalline succinate hydrate of claim 7, wherein the crystalline succinate hydrate is characterized by a powder X-ray diffraction pattern comprising diffraction peaks at 2θ values of 4.81±0.20, 9.66±0.20, 14.93±0.20, and 16.78±0.20.

9. The crystalline succinate hydrate of claim 8 wherein the powder X-ray diffraction pattern is further characterized by having two or more additional diffraction peaks at 2θ values selected from 10.46±0.20, 16.21±0.20, 17.45±0.20, 22.87±0.20, and 24.77±0.20.

10. The crystalline succinate hydrate of claim 7, wherein the crystalline succinate hydrate is characterized by a powder X-ray diffraction pattern in which the peak positions are substantially in accordance with the peak positions of the pattern shown in FIG. 5.

11. The crystalline succinate hydrate of claim 7 wherein the crystalline succinate hydrate is characterized by a differential scanning calorimetry trace recorded at a heating rate of 10° C. per minute which shows a maximum in endothermic heat flow at a temperature between 180° C. and 190° C.

12. The crystalline succinate hydrate of claim 7, wherein the crystalline succinate hydrate is characterized by a differential scanning calorimetry trace substantially in accordance with that shown in FIG. 6.

13. A pharmaceutical composition comprising the crystalline oxalate hydrate of claim 2 or the crystalline succinate hydrate of claim 8, and a pharmaceutically-acceptable carrier.

14. A method of preparing a crystalline hydrate of the oxalate salt of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol, the method comprising:
 (a) dissolving a 1:1 mixture of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol: oxalic acid in a 1:1 mixture of tetrahydrofuran:water at room temperature,
 (b) adding a 1:1:2 mixture of tetrahydrofuran:water:acetonitrile to produce a suspension,
 (c) stirring the suspension for about one day, and
 (d) isolating the crystalline hydrate of the oxalate salt from the suspension.

15. A method of treating a respiratory disease in a mammal, the method comprising administering to the mammal a pharmaceutical composition comprising the crystalline oxalate hydrate of claim 2 or the crystalline succinate hydrate of claim 8, and a pharmaceutically-acceptable carrier.

16. The method of claim 15 wherein the respiratory disease is asthma, chronic obstructive pulmonary disease, cystic fibrosis, pneumonitis, idiopathic pulmonary fibrosis, acute lung injury, acute respiratory distress syndrome, bronchitis, emphysema or bronchiolitis obliterans.

17. The method of claim 15 wherein the respiratory disease is bronchiolitis obliterans.

18. The method of claim 15 wherein the respiratory disease is asthma or chronic obstructive pulmonary disease.

19. The method of claim 18 wherein the respiratory disease is asthma.

20. The method of claim 15 wherein the pharmaceutical composition is administered by inhalation.

21. The method of claim 15 wherein the respiratory disease is a lung infection, a helminthic infection, pulmonary arterial hypertension, sarcoidosis, lymphangioleiomyomatosis, bronchiectasis, or infiltrative pulmonary disease.

22. The method of claim 15 wherein the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, or immune-checkpoint-inhibitor induced pneumonitis.

23. A method of treating an ocular disease in a mammal, the method comprising administering to the eye of the mammal a pharmaceutical composition comprising the crystalline oxalate hydrate of claim 2 or the crystalline succinate hydrate of claim 8, and a pharmaceutically-acceptable carrier.

* * * * *

UNITED STATES PATENT AND TRADEMARK OFFICE
CERTIFICATE OF CORRECTION

PATENT NO. : 10,251,874 B2
APPLICATION NO. : 15/966452
DATED : April 9, 2019
INVENTOR(S) : Dabros et al.

Page 1 of 1

It is certified that error appears in the above-identified patent and that said Letters Patent is hereby corrected as shown below:

In the Claims

At Column 34, Line 34, "1H-imidazo" should be "1*H*-imidazo";

At Column 34, Line 34, "1H-indazol" should be "1*H*-indazol";

At Column 34, Line 37, "20" should be "2θ";

At Column 34, Line 42, "20" should be "2θ";

At Column 34, Line 61, "1H-imidazo" should be "1*H*-imidazo";

At Column 34, Line 61, "1H-indazol" should be "1*H*-indazol";

At Column 34, Line 66, "20" should be "2θ";

At Column 35, Line 3, "20" should be "2θ";

At Column 35, Line 28, "1H-imidazo" should be "1*H*-imidazo";

At Column 35, Line 29, "1H-indazol" should be "1*H*-indazol";

At Column 35, Lines 31-32, "1H-imidazo" should be "1*H*-imidazo";

At Column 35, Line 32, "1H-indazol" should be "1*H*-indazol".

Signed and Sealed this
Eighteenth Day of June, 2019

Andrei Iancu
*Director of the United States Patent and Trademark Office*